(12) United States Patent
Lim et al.

(10) Patent No.: US 8,323,676 B2
(45) Date of Patent: *Dec. 4, 2012

(54) POLY(ESTER-AMIDE) AND POLY(AMIDE) COATINGS FOR IMPLANTABLE MEDICAL DEVICES FOR CONTROLLED RELEASE OF A PROTEIN OR PEPTIDE AND A HYDROPHOBIC DRUG

(75) Inventors: Florencia Lim, Union City, CA (US); Mikael O. Trollsas, San Jose, CA (US); Xinmin Xu, Libertyville, IL (US); Bozena Zofia Maslanka, Aptos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 847 days.

This patent is subject to a terminal disclaimer.

(21) Appl. No.: 12/165,521

(22) Filed: Jun. 30, 2008

(65) Prior Publication Data

US 2009/0324672 A1     Dec. 31, 2009

(51) Int. Cl.
*A61F 2/02* (2006.01)
*C07D 491/16* (2006.01)
(52) U.S. Cl. .................................... 424/423; 514/291
(58) Field of Classification Search .................... None
See application file for complete search history.

(56) References Cited

U.S. PATENT DOCUMENTS

| | | | |
|---|---|---|---|
| 4,293,539 A | 10/1981 | Ludwig et al. | |
| 4,304,767 A | 12/1981 | Heller et al. | |
| 4,622,244 A | 11/1986 | Lapka et al. | |
| 4,733,665 A | 3/1988 | Palmaz | |
| 4,800,882 A | 1/1989 | Gianturco | |
| 4,886,062 A | 12/1989 | Wiktor | |
| 4,897,268 A | 1/1990 | Tice et al. | |
| 4,954,298 A | 9/1990 | Yamamoto et al. | |
| 5,208,324 A | 5/1993 | Klaveness et al. | |
| 5,383,928 A | 1/1995 | Scott et al. | |
| 5,419,760 A | 5/1995 | Narciso, Jr. | |
| 5,575,815 A | 11/1996 | Slepian et al. | |
| 5,581,387 A | 12/1996 | Cahill | |
| 5,607,475 A | 3/1997 | Cahalan et al. | |
| 5,646,160 A | 7/1997 | Morris et al. | |
| 5,725,568 A | 3/1998 | Hastings | |
| 5,782,908 A | 7/1998 | Cahalan et al. | |
| 5,843,156 A | 12/1998 | Slepian et al. | |
| 5,861,387 A | 1/1999 | Labrie et al. | |
| 5,874,165 A | 2/1999 | Drumheller | |
| 5,880,220 A * | 3/1999 | Warzelhan et al. | 525/424 |
| 5,891,192 A | 4/1999 | Murayama et al. | |
| 5,897,955 A | 4/1999 | Drumheller | |
| 5,914,182 A | 6/1999 | Drumheller | |
| 6,015,815 A | 1/2000 | Mollison | |
| 6,087,479 A | 7/2000 | Stamler et al. | |
| 6,153,252 A | 11/2000 | Hossainy et al. | |
| 6,174,539 B1 | 1/2001 | Stamler et al. | |
| 6,224,794 B1 | 5/2001 | Amsden et al. | |
| 6,277,927 B1 | 8/2001 | Roby et al. | |
| 6,290,729 B1 | 9/2001 | Slepian et al. | |
| 6,329,386 B1 | 12/2001 | Mollison | |
| 6,379,379 B1 | 4/2002 | Wang | |
| 6,379,382 B1 | 4/2002 | Yang | |
| 6,451,373 B1 | 9/2002 | Hossainy et al. | |
| 6,471,978 B1 | 10/2002 | Stamler et al. | |
| 6,497,729 B1 | 12/2002 | Moussy et al. | |
| 6,503,538 B1 * | 1/2003 | Chu et al. | 424/497 |
| 6,506,408 B1 | 1/2003 | Palasis | |
| 6,514,734 B1 | 2/2003 | Clapper et al. | |
| 6,528,093 B1 | 3/2003 | Kamei et al. | |
| 6,548,637 B1 | 4/2003 | Persons et al. | |
| 6,585,764 B2 | 7/2003 | Wright et al. | |
| 6,613,082 B2 | 9/2003 | Yang | |
| 6,613,084 B2 | 9/2003 | Yang | |
| 6,616,765 B1 * | 9/2003 | Castro et al. | 118/669 |
| 6,623,521 B2 | 9/2003 | Steinke et al. | |
| 6,652,575 B2 | 11/2003 | Wang | |
| 6,703,040 B2 | 3/2004 | Katsarava et al. | |
| 6,746,773 B2 | 6/2004 | Llanos et al. | |
| 6,767,637 B2 | 7/2004 | Park et al. | |
| 7,048,947 B2 | 5/2006 | Kamei et al. | |
| 7,056,591 B1 | 6/2006 | Pacetti et al. | |
| 7,060,299 B2 | 6/2006 | Alavattam et al. | |
| 7,063,884 B2 | 6/2006 | Hossainy et al. | |
| 7,166,680 B2 | 1/2007 | DesNoyer et al. | |
| 7,202,325 B2 | 4/2007 | Hossainy et al. | |
| 7,208,010 B2 | 4/2007 | Shanley et al. | |
| 7,220,816 B2 | 5/2007 | Pacetti et al. | |
| 7,247,313 B2 | 7/2007 | Roorda et al. | |
| 7,910,152 B2 | 3/2011 | Kleiner et al. | |
| 2001/0027340 A1 | 10/2001 | Wright et al. | |
| 2002/0015720 A1 | 2/2002 | Katsarava et al. | |
| 2003/0129130 A1 | 7/2003 | Guire et al. | |
| 2004/0033251 A1 | 2/2004 | Sparer et al. | |
| 2004/0073297 A1 | 4/2004 | Rohde et al. | |

(Continued)

FOREIGN PATENT DOCUMENTS

EP     0 778 250     6/1997

(Continued)

OTHER PUBLICATIONS

Blindt et al. "A Novel Drug-Eluting Stent Coated with an Integrin-Binding Cyclic Arg-Gly-Asp peptide Inhibits Neointimal Hyperplasia by Recruiting Endothelial Progenitor Cells", J. of the Am. College of Cardiology vol. 47, No. 9, pp. 1786-1795 (2006).*

(Continued)

*Primary Examiner* — Robert A Wax
*Assistant Examiner* — Danah Al-Awadi
(74) *Attorney, Agent, or Firm* — Squire Sanders (US) LLP

(57) ABSTRACT

This invention is generally related to coatings for implantable medical devices, such as drug delivery vascular stents. The coating includes a drug reservoir layer above the outer surface of the device body, the drug reservoir layer with a peptide or protein, a hydrophobic drug, and a polymer with a weight average molecular weight between about 10,000 to about 150,000 Daltons. A preferred polymer is a poly(ester amide) polymer.

32 Claims, 4 Drawing Sheets

U.S. PATENT DOCUMENTS

| | | |
|---|---|---|
| 2004/0106985 A1 | 6/2004 | Jang |
| 2004/0170685 A1 | 9/2004 | Carpenter et al. |
| 2004/0172121 A1 | 9/2004 | Eidenschink et al. |
| 2004/0172127 A1 | 9/2004 | Kantor |
| 2004/0228831 A1 | 11/2004 | Belinka et al. |
| 2004/0236415 A1 | 11/2004 | Thomas |
| 2005/0008671 A1 | 1/2005 | Van Antwerp |
| 2005/0084515 A1 | 4/2005 | Udipi et al. |
| 2005/0095267 A1 | 5/2005 | Campbell et al. |
| 2005/0106204 A1 | 5/2005 | Hossainy et al. |
| 2005/0112171 A1 | 5/2005 | Tang et al. |
| 2005/0131201 A1 | 6/2005 | DesNoyer et al. |
| 2005/0137381 A1 | 6/2005 | Pacetti et al. |
| 2005/0137715 A1 | 6/2005 | Phan et al. |
| 2005/0147647 A1 | 7/2005 | Glauser et al. |
| 2005/0181015 A1 | 8/2005 | Zhong |
| 2005/0208091 A1 | 9/2005 | Pacetti |
| 2005/0208093 A1 | 9/2005 | Glauser et al. |
| 2005/0233062 A1 | 10/2005 | Hossainy et al. |
| 2005/0245637 A1* | 11/2005 | Hossainy et al. ............ 523/113 |
| 2005/0265960 A1 | 12/2005 | Pacetti et al. |
| 2005/0271700 A1 | 12/2005 | DesNoyer et al. |
| 2005/0283229 A1 | 12/2005 | Dugan et al. |
| 2005/0288481 A1* | 12/2005 | DesNoyer et al. ............ 528/310 |
| 2006/0089485 A1 | 4/2006 | DesNoyer et al. |
| 2006/0093842 A1 | 5/2006 | DesNoyer et al. |
| 2006/0115513 A1 | 6/2006 | Hossainy |
| 2006/0142541 A1 | 6/2006 | Hossainy |
| 2006/0147412 A1 | 7/2006 | Hossainy et al. |
| 2006/0198870 A1 | 9/2006 | Mollison et al. |
| 2007/0003589 A1 | 1/2007 | Astafieva et al. |
| 2007/0190103 A1 | 8/2007 | Hossainy et al. |
| 2007/0202147 A1 | 8/2007 | Kleiner et al. |
| 2007/0280991 A1 | 12/2007 | Glauser et al. |
| 2007/0293941 A1 | 12/2007 | Gale et al. |
| 2008/0014236 A1 | 1/2008 | Pacetti et al. |
| 2008/0014241 A1 | 1/2008 | Desnoyer et al. |
| 2008/0145402 A1 | 6/2008 | Mollison et al. |
| 2009/0258028 A1 | 10/2009 | Glauser et al. |
| 2009/0324671 A1 | 12/2009 | Ngo et al. |
| 2010/0047319 A1 | 2/2010 | Ngo et al. |
| 2011/0151104 A1 | 6/2011 | Kleiner et al. |
| 2011/0153004 A1 | 6/2011 | Kleiner et al. |
| 2011/0200660 A1 | 8/2011 | Kleiner et al. |
| 2011/0311596 A1 | 12/2011 | Ngo et al. |

FOREIGN PATENT DOCUMENTS

| | | |
|---|---|---|
| EP | 1 795 185 | 6/2007 |
| WO | WO 94/09010 | 4/1994 |
| WO | WO 2005/092406 | 10/2005 |
| WO | WO 2006/112932 | 10/2006 |
| WO | WO 2010/002584 | 1/2010 |

OTHER PUBLICATIONS

U.S. Appl. No. 10/816,072, filed Mar. 31, 2004, Dugan et al.
U.S. Appl. No. 12/165,173, filed Jun. 30, 2008, Ngo et al.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Lee et al., *In-vivo biocompatibility evaluation of stents coated with a new biodegradable elastomeric and functional polymer*, Coron. Artery. Dis., 13(4): (2002) pp. 237-241.
Moreno et al., *Macrophage Infiltration Predicts Restenosis After Coronary Intervention in Patients with Unstable Angina*, Circulation, vol. 94, No. 12, (1996) pp. 3098-3102.
Oikawa et al., *Mechanisms of Acute Gain and Late Lumen Loss After Atherectomy in Different Preintervention Arterial Remodeling Patterns*, The Am. J. of Cardiology, vol. 89, (2002) pp. 505-510.
Scully et al., *Effect of a heparan sulphate with high affinity for antithrombin III upon inactivation of thrombin and coagulaton Factor Xa*, Biochem J. 262, (1989) pp. 651-658.
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
International Search Report for PCT/US2007/013327, filed May 6, 2007, mailed Nov. 30, 2007, 14 pgs.
Blindt, "Abciximab Inhibits the Migration and Invasion Potential of Human Coronary Artery Smooth Muscle Cells", J. Mol. Cell. Cardiol. vol. 32, pp. 2195-2206 (2000).
Coller, "Anti-GPIIb/IIIa Drugs: Current Strategies and Future Directions", Thromb. Haemost. vol. 86, pp. 427-443 (2001).
Fittkau et al., "The selective modulation of endothelial cell mobility on RGD peptide containing surfaces by YIGSR peptides", Biomaterials vol. 26, pp. 167-174 (2005).
Kouvroukoglou et al., "Endothelial cell migration on surfaces modified with immobilized adhesive peptides", Biomaterials vol. 21, pp. 1725-1733 (2000).
Mann et al., "Cell adhesion peptides alter smooth muscle cell adhesion, proliferation, migration, and matrix protein synthesis on modified surfaces and in polymer scaffolds", J. Biomed. Mater. Res. vol. 60, pp. 86-93 (2002).
Sajid et al., "$\alpha_v\beta_3$—Integrin antagonists inhibit thrombin-induced proliferation and focal adhesion formation in smooth muscle cells", Am. J. Physiol. Cell Physiol. 285, pp. C1330-C1338 (2003).
Srivastva et al., "Selective α v β3 integrin blockade potently limits neointimal hyperplasia and lumen stenosis following deep coronary arterial stent injury. Evidence for the functional importance of integrin α v β3 and osteopontin expression during neointima formation", Cardiovasc. Res. vol. 36 pp. 408-428 (1997).
UNOXOL™ Diol-The New Building Block for Coating, Dow Chem. Co. Product Information (2011) 1 pg.
U.S. Appl. No. 12/196,143, filed Aug. 21, 2008, Ngo et al.
U.S. Appl. No. 12/424,489, filed Apr. 15, 2009, Glauser et al.
U.S. Appl. No. 13/221,767, filed Aug. 30, 2011, Ngo et al.
Fitzgerald et al. "Investigation of the mechanisms governing the release of levamisole from poly-lactide-co-glycolide delivery systmens", Journal of Controlled release 42:125-132 (1996).
Frank et al. "Controlled release from bioerodible polymers: effect of drug type and polymer composition", Journal of Controlled Release 102:333-344 (2005).
Kipshidze et al., "Role of the endothelium in modulating neointimal formation", J. of Am. Coll. of Cardiology vol. 44, No. 4, pp. 733-739 (2004).
Serruys et al., "A Randomizad comparison of the value of additional stenting after optimal balloon angioplasty for long coronary lesions", J. of Am. Coll. of Cardiology vol. 39, No. 3, pp. 393-399 (2002).
Sigma-aldrich.com (Paclitaxel).

* cited by examiner

POLY(ESTER-AMIDE) AND POLY(AMIDE) COATINGS FOR IMPLANTABLE MEDICAL DEVICES FOR CONTROLLED RELEASE OF A PROTEIN OR PEPTIDE AND A HYDROPHOBIC DRUG

BACKGROUND

1. Field of the Invention

This invention is generally related to coatings for implantable medical devices, such as drug delivery vascular stents.

2. Description of the State of the Art

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of the arterial lining and to reduce the chance of thrombosis or restenosis, a stent is implanted in the artery to keep the artery open.

Drug delivery stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, ISR still poses a significant problem given the large volume of coronary interventions and their expanding use. The pathophysiological mechanism of ISR involves interactions between the cellular and acellular elements of the vessel wall and the blood. Damage to the endothelium during PCI constitutes a major factor for the development of ISR (see, e.g., Kipshidze, N., et al., J. Am. Coll. Cardiol. 44:733-739 (2004)).

The embodiments of the present invention relate to drug delivery stents, as well as others embodiments that are apparent to one having ordinary skill in the art.

SUMMARY

Various embodiments of the present invention include an implantable medical device including a device body and a coating disposed over the device body. The coating includes a drug reservoir layer including a peptide or protein, a hydrophobic drug, and a polymer with a weight average molecular weight between about 10 to about 150 K Daltons. The mass ratio of the peptide or protein to the hydrophobic drug is from about 1:0.1 to about 1:10, and the mass ratio of the protein or peptide to the polymer is from about 1:0.1 to about 1:10. The cumulative release of the peptide or protein from the drug reservoir layer is between about 5% and about 50% at 24 hours and between about 10% and about 95% at 7 days.

In an aspect of the invention, the cumulative release of the hydrophobic drug from the drug reservoir layer is between about 5% and about 50% at 24 hours and between about 10% and about 95% at 7 days.

In an aspect of the invention, the cumulative release of the hydrophobic drug from the drug reservoir layer is between about 10% and about 35% at 24 hours and between about 25% and about 75% at 7 days.

In an aspect of the invention, the mass ratio of the peptide or protein to the hydrophobic drug is from about 1:0.2 to 1:5.

In an aspect of the invention, the mass ratio of the peptide or protein to the hydrophobic drug is from about 1:0.5 to 1:3.

In an aspect of the invention, the mass ratio of the protein or peptide to the polymer is from about 1:0.2 to about 1:5.

In an aspect of the invention, the mass ratio of the protein or peptide to the polymer is from about 1:2 to about 1:4.

In an aspect of the invention, the polymer is selected from the group consisting of poly(amide) polymers, poly(ester-amide) polymers, phosphorylcholine substituted polymers such as poly(ester-amide)s, polyacrylates, and polymethacrylates, PC1036, and combinations thereof.

In some embodiments, the polymer is poly(ester-amide) or poly(amide) polymer. In some embodiments, the poly(ester amide) polymer is a random copolymer with two or more constitutional units.

In an aspect of the invention, the polymer is a poly(ester-amide) or a poly(amide) that is of the following formula:

$$\left[ -(A_i-B_j)_{x_n} \diagup (A_i-C_k)_{y_m} - \right]_p \quad (M_w, s_i, t_j, v_k)$$

wherein i is an integer from 1 to 10, inclusive;
j is an integer from 0 to 10, inclusive;
k is an integer from 0 to 15, inclusive;
$x_n$ is an integer from 0 to 100, inclusive;
$y_m$ is an integer from 0 to 150, inclusive;
p is an integer from 2 to about 4500;
$M_w$ is from about 10,000 to about 1,000,000 Da;
$s_i$ is a number from 0 to 0.5, inclusive;
$t_j$ is a number from 0 to 0.5, inclusive;
$v_k$ is a number from 0 to 0.5, inclusive;
with the proviso that $$\Sigma_i s_i + \Sigma_j t_j + \Sigma_k v_k = 1.0;$$

$$\Sigma_i s_i = \Sigma_j t_j + \Sigma_k v_k = 0.5;$$

$$\Sigma_i s_i > 0;$$

$$\Sigma_j t_j > 0 \text{ or } \Sigma_k v_k > 0;$$

each $A_i$ has the chemical structure:

$$-\overset{O}{\underset{\|}{C}}-(R_{ai})-\overset{O}{\underset{\|}{C}}-;$$

each $B_j$ has the chemical structure $$-\overset{H}{\underset{|}{N}}-\overset{H}{\underset{|}{\underset{R_{bj}}{C}}}-\overset{O}{\underset{\|}{C}}-O-(R_{cj})-O-\overset{O}{\underset{\|}{C}}-\overset{H}{\underset{|}{\underset{R_{bj'}}{C}}}-\overset{}{\underset{H}{N}}-;$$

and
each $C_k$ has the chemical structure:

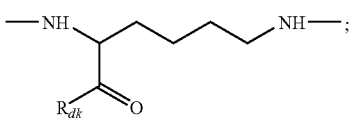

wherein:
each $R_{bj}$, and $R_{bj'}$ are independently selected from the group consisting of hydrogen and (C1-C4)alkyl, wherein:
the alkyl group is optionally substituted with a moiety selected from the group consisting of —OH, —SH, —SeH, —C(O)OH, —NHC(NH)NH$_2$,

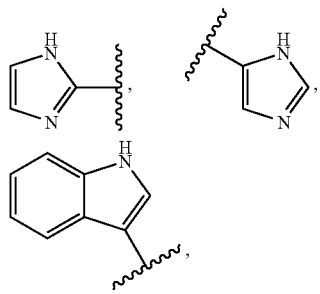

phenyl and

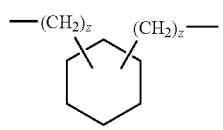

or
one or more of $R_{bj}$ and $R_{bj'}$ may form a bridge between the carbon to which it is attached and the adjacent nitrogen, the bridge comprising —CH$_2$CH$_2$CH$_2$—;
each $R_{ai}$ and each $R_{cj}$ are independently selected from the group consisting of (C1-C12)alkyl, (C2-C12)alkenyl, (C3-C8)cycloalkyl, —(CH$_2$CH$_2$O)$_q$CH$_2$CH$_2$— wherein q is an integer from 1 to 10, inclusive, and

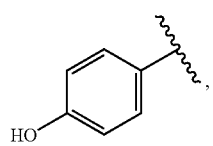

where z is 0, 1, or 2;
$R_{dk}$ is selected from the group consisting of —H, —OH, —O(C1-C20)alkyl, —O(C1-C20)alkenyl and —O(CH$_2$CH$_2$O)$_w$CH$_2$CH$_2$OR$_{ek}$, wherein:
w is an integer from 1 to 600, inclusive;
$R_{ek}$ is selected from the group consisting of hydrogen, —C(O)CH=CH$_2$ and —C(O)C(CH$_3$)=CH$_2$; and,
each $R_{ai}$ corresponds to the i$^{th}$ $A_i$ group, each $R_{bj}$, $R_{bj'}$, and $R_{cj}$ corresponds to the j$^{th}$ $B_j$ group, and each $R_{dk}$ and optionally $R_{ek}$ correspond to the k$^{th}$ $C_k$ group.

In an aspect of the invention, for the polymer i=1, j=2, k=0, and each of $R_{a1}$ is selected from the group consisting of —(CH$_2$)$_6$—, —(CH$_2$)$_7$—, —(CH$_2$)$_8$—, —(CH$_2$)$_9$—, and —(CH$_2$)$_{10}$—; each of $R_{b1}$, $R_{b1'}$, $R_{b2}$ and $R_{b2'}$ are the same, and are selected from the group consisting of —(CH$_2$)—(CH(CH$_3$)$_2$) and —(CH$_3$); $R_{c1}$ is selected from the group consisting of —(CH$_2$)$_4$, —(CH$_2$)$_5$—, —(CH$_2$)$_6$—, —(CH$_2$)$_7$—, and —(CH$_2$)$_8$—; and $R_{c2}$ is selected from the group consisting of

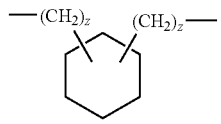

where z is 0, 1, or 2.
In an aspect of the invention, $R_{c2}$ is selected from the group consisting of

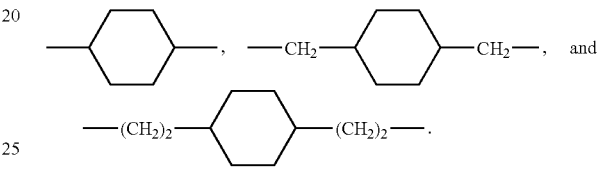

In an aspect of the invention, for the poly(ester-amide) $R_{a1}$ is —(CH$_2$)$_8$—; $R_{b1}$, $R_{b1'}$, $R_{b2}$ and $R_{b2'}$ the same and are —(CH$_2$)—(CH(CH$_3$)$_2$); $R_{c1}$ is —(CH$_2$)$_6$—; $R_{c2}$ is

and $s_1$ is 0.5, and $t_1$ is between 0.125 and 0.375.

In an aspect of the invention, the hydrophobic drug is selected from the group consisting of sirolimus (rapamycin), biolimus A9, deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin, 40-O-[2-(2-hydroxy)ethoxy]ethyl-rapamycin, 40-O-tetrazole-rapamycin, 40-O-tetrazolylrapamycin, 40-epi-(N1-tetrazole)-rapamycin, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), dexamethasone, γ-hiridun, clobetasol, dexamethasone acetate, mometasone, imatinib mesylate, midostaurin, feno fibrate, feno fibric acid, and prodrugs thereof, co-drugs thereof, and combinations thereof.

In an aspect of the invention, the hydrophobic drug is everolimus.

In an aspect of the invention, the hydrophobic drug is zotarolimus.

In an aspect of the invention, the hydrophobic drug is an anti-proliferative.

In an aspect of the invention, the peptide or protein is a selected from the group consisting of cRGD, other similar size peptides and combinations thereof.

In an aspect of the invention, the peptide or protein is selected from the group consisting of RGD, an RGD peptide, a cyclic RGD peptide (cRGD), a synthetic cyclic RGD (cRGD) mimetic, or a synthetic RGD mimetic and combinations thereof.

In an aspect of the invention, the peptide or protein is cRGD.

In an aspect of the invention, the peptide or protein is cRGD, and the hydrophobic drug is everolimus.

In an aspect of the invention, the drug reservoir layer is between about 0.5 and about 9 µm in thickness.

In an aspect of the invention, the mass ratio of (protein or peptide):hydrophobic drug:polymer is about 1:1:3.

Various embodiments of the present invention include an implantable medical device including a device body and a coating disposed over the device body. The coating includes a drug reservoir layer including a peptide or protein, a hydrophobic drug, a polymer with a weight average molecular weight between about 10 to about 150 K Daltons. The mass ratio of the peptide or protein to the hydrophobic drug is about 1:0.1 to about 1:10, and the ratio of the sum of the mass of peptide or protein and the mass of the hydrophobic drug to the mass of the polymer is about 1:1 to about 1:12. The drug reservoir layer thickness is between about 0.5 and about 7 µm in thickness. The polymer is poly(ester-amide) that is a random copolymer having the formula:

$$\left[ (A_1\text{-}B_1)_{x1} \middle| (A_1\text{-}B_2)_{x2} \right]_p \quad (Mw, s_1, t_1, t_2)$$

wherein:
$A_1$ has the chemical structure:

$$-\overset{O}{\underset{}{C}}-(R_{ai})-\overset{O}{\underset{}{C}}-;$$

each of $B_1$ and $B_2$ has the chemical structure $$-\overset{H}{N}-\overset{H}{\underset{R_{bj}}{C}}-\overset{O}{\underset{}{C}}-O-(R_{cj})-O-\overset{O}{\underset{}{C}}-\overset{H}{\underset{R_{bj'}}{C}}-\overset{}{\underset{H}{N}}-;$$

$t_1$ is between 0.125 and 0.375;
$t_2 = 0.5 - t_1$;
$s_1 = 0.5$; and
p is an integer from 2 to about 4500;
wherein:
$R_{a1}$ is selected from the group consisting of —$(CH_2)_6$—, —$(CH_2)_7$—, —$(CH_2)_8$—, —$(CH_2)_9$—, and —$(CH_2)_{10}$—; each of $R_{b1}$ $R_{b1'}$, $R_{b2}$ and $R_{b2'}$ are the same, and are selected from the group consisting of —$(CH_2)$—$(CH(CH_3)_2)$ and —$(CH_3)$; $R_{c1}$ is selected from the group consisting of —$(CH_2)_4$—, —$(CH_2)_5$—, —$(CH_2)_6$—, —$(CH_2)_7$—, and —$(CH_2)_8$—; and $R_{c2}$ is selected from the group consisting of $$-(CH_2)_z\underset{}{\diagdown}\underset{\bigcirc}{}\diagup(CH_2)_z-$$

where z is 0, 1, or 2.

Various embodiments of the present invention include an implantable medical device including a device body and a coating disposed over the device body. The coating includes a drug reservoir layer including a peptide or protein, a hydrophobic drug, and a random copolymer. The mass ratio of the (peptide or protein):hydrophobic drug:polymer is about 1:1:3. The drug reservoir layer thickness is between about 0.5 and about 7 µm in thickness. The random copolymer has a weight average molecular weight between about 10 to about 150 kD of the formula:

$$\left[ (A_1\text{-}B_1)_{x1} \middle| (A_1\text{-}B_2)_{x2} \right]_p \quad (Mw, s_1, t_1, t_2)$$

wherein:
$A_1$ has the chemical structure:

$$-\overset{O}{\underset{}{C}}-(R_{ai})-\overset{O}{\underset{}{C}}-;$$

each of $B_1$ and $B_2$ has the chemical structure $$-\overset{H}{N}-\overset{H}{\underset{R_{bj}}{C}}-\overset{O}{\underset{}{C}}-O-(R_{cj})-O-\overset{O}{\underset{}{C}}-\overset{H}{\underset{R_{bj'}}{C}}-\overset{}{\underset{H}{N}}-;$$

$t_1$ is between 0.125 and 0.375;
$t_2 = 0.5 - t_1$;
$s_1 = 0.5$; and
p is an integer from 2 to about 4500;
wherein:
$R_{a1}$ is, —$(CH_2)_8$—; each of $R_{b1}$ $R_{b1'}$, $R_{b2}$ and $R_{b2'}$ are the same, and are —$(CH_2)$—$(CH(CH_3)_2)$; $R_{c1}$ is —$(CH_2)_6$—; and $R_{c2}$ is $$-\underset{\bigcirc}{\diagdown\diagup}-.$$

Various embodiments of the present invention include a method of fabricating a coated implantable medical device. The method includes the operations of: providing an implantable medical device; providing a peptide or protein, a hydrophobic drug, and a polymer with a weight average molecular weight between about 10,000 to about 150,000 Daltons; dissolving or dispersing the peptide or protein, the hydrophobic drug, and the polymer in ethanol wherein the mass ratio of the peptide or protein to the hydrophobic drug is from about 1:0.1 to about 1:10; and wherein the mass ratio of the protein or peptide to the polymer is from about 1:0.1 to about 1:10; applying the ethanol solution to the implantable medical device; and removing the ethanol to form a drug reservoir layer. The cumulative release of the peptide or protein from the drug reservoir layer is between about 5% and about 50% at 24 hours and between about 10% and about 95% at 7 days.

In an aspect of the invention, wherein for the coating produced by the method the cumulative release of the hydrophobic drug from the drug reservoir layer is between about 5% and about 50% at 24 hours and between about 10% and about 95% at 7 days.

In an aspect of the invention, wherein for the coating produced by the method the cumulative release of the hydrophobic drug from the drug reservoir layer is between 10% and about 35% at 24 hours and between about 25% and about 75% at 7 days.

In an aspect of the invention is a coated implantable medical device fabricated by the methods above.

In an aspect of the invention, the implantable medical device is a stent.

Any drugs or active agents having anti-proliferative effects can be used in the present invention. The anti-proliferative active agent can be a natural proteineous agent such as a cytotoxin or a synthetic molecule. Active agents included, without limitation, are anti-proliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs, macrolide antibiotics (such as without limitation rapamycin), FKBP-12 mediated mTOR inhibitors, perfenidone, prodrugs thereof, co-drugs thereof, and combinations thereof.

In some embodiments, the hydrophobic drug has a solubility in ethanol of no greater than 25 mg/ml.

In some embodiments, the polymer with a weight average molecular weight between about 10,000 to about 150,000 Daltons and has a solubility in ethanol of at least 500 mg/ml or greater.

In some embodiments, the mass ratio of the peptide or protein to the hydrophobic drug is about 0.2:1 to about 2:1.

In some embodiments, the mass ratio of the sum of the mass of peptide or protein and the mass of the hydrophobic drug to the mass of the polymer is about 1:1 to about 1:12, preferably 1:2 to 1:4.

DETAILED DESCRIPTION

Figure 1:
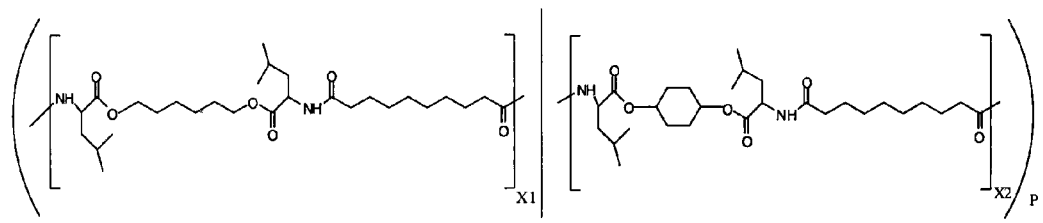
FIG. 1 is the structure of a poly(ester amide) polymer utilized in some embodiments of the present invention.

Provided herein is a coating layer capable of controlled release of at least one hydrophilic peptide or protein (e.g., cRGD peptide) and at least one hydrophobic drug, such as without limitation, an anti-proliferative drug, from one coating layer. In some embodiments, the hydrophilic drug is a cRGD peptide while the hydrophobic drug is an anti-proliferative drug such as everolimus. cRGD is a hydrophilic chemo-attractant for endothelial progenitor cells (EPCs). The anti-proliferative such as everolimus can reduce the incidence of resteonosis.

In some embodiments the cumulative release of at least one of the hydrophilic peptides or proteins may be not less than 5% and not more than 50% at 24 hours (or between about 5% and about 50% at 24 hours), and not less than 10% and not more than about 95% at 7 days (or between about 10% and about 95% at 7 days). In some embodiments, the cumulative release of the hydrophobic drug from the drug reservoir layer is between about 5% and about 50% at 24 hours, and between about 10% and about 90% at 7 days. In some embodiments, both cumulative release profiles are applicable to the drug reservoir layer.

In some embodiments, at least one of the polymers in at least one of the coating layers including a protein or peptide and a hydrophobic drug (drug reservoir layer) may be one which is soluble in ethanol, while in other embodiments, all polymers in at least one drug reservoir layer may be soluble in ethanol. In some embodiments, at least one polymer may be a poly(ester-amide) or poly(amide) polymers. In some embodiments, the coating layer, including at least one hydrophilic protein or peptide and at least one hydrophobic drug, is the only coating layer on the implantable medical device. In some embodiments, the implantable medical device is a stent.

In some embodiments, the coating layer can further include a drug that is not the hydrophilic drug (a peptide or a protein), or the hydrophobic drug described above.

Delivery of both a peptide or protein and a hydrophobic drug (both drugs) from one layer (drug reservoir layer) provides several advantages. First, fewer manufacturing operations are required if both drugs may be included in one coating layer, resulting in a savings in time, money, and materials. Second, multiple layers will generally result in a thicker overall coating. Thus, a single coating layer may allow for a thinner stent profile. In general thinner coatings resulted in better inflammatory response. Third, a coating layer above a drug reservoir layer will impact the release of the drugs in the layer below, and therefore, formulation and manufacture, of such multiple layer systems may be more complex.

The coating layers of the various embodiments of the present invention result in controlled delivery of both drugs due in part to the selection of the appropriate polymer. In particular, a polymer that is soluble in ethanol combined with a hydrophobic drug that is soluble in ethanol, allows for the application of a coating layer on a substrate which includes a peptide or protein and a hydrophobic drug. In other embodiments a polymer is chosen that is soluble in another solvent in which both the hydrophobic drug and the protein or peptide are soluble.

Definitions

As used herein, unless specified otherwise, any words of approximation such as without limitation, "about," "essentially," "substantially" and the like mean that the element so modified need not be exactly what is described, but can vary from the description by as much as ±15% without exceeding the scope of this invention.

As used herein, any ranges presented are inclusive of the end-points. For example, the statement "a temperature between 10° C. and 30° C." includes 10° C. and 30° C., as well as any temperature in between.

As used herein, an "implantable medical device" refers to any type of device that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, cerebrospinal fluid shunts, and intrauterine devices. An implantable medical device specifically designed and intended solely for the localized delivery of a drug is within the scope of this invention.

As used herein with respect to an implantable medical device, "device body," refers to an implantable medical device in a fully formed utilitarian state with an outer surface to which no coating or layer of material different from that of which the device is manufactured has been applied. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of.

A type of implantable medical device is a "stent." A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (m, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

As used herein, "therapeutic agent," "drug," "active agent," or "bioactive agent," which will be used interchangeably, refers to any substance that, when administered in a therapeutically effective amount to a patient suffering from a disease or condition, has a therapeutic beneficial effect on the health and well-being of the patient. A therapeutic beneficial effect on the health and well-being of a patient includes, but it not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "therapeutic agent," "drug" or "active agent," or "bioactive agent" also encompasses salts, esters, amides, prodrugs, active metabolites, analogs, and the like.

As used herein, a "peptide" will refer to a molecule comprising from 2 to 49 amino acids. Herein, chains of 50 amino acids or more are referred to as "proteins." Both peptides and proteins may be classified as drugs if the peptide or protein has a therapeutic effect. Not all peptides and proteins are also classified as drugs.

As used herein, a "polymer" is a molecule made up of the repetition of a simpler unit, herein referred to as a repeat unit. The repeat units themselves can be the product of the reactions of other compounds. A polymer may comprise one or more types of repeat units. As used herein, the term polymer refers to a molecule comprising 2 or more repeat units. A "monomer" is compound which may be reacted to form a polymer, or part of a polymer, but is not itself the repetition of a simpler unit. A monomer is not equivalent to a repeat unit, but is related to a repeat unit. As a non-limiting example, $CH_2\!\!=\!\!CH_2$ or ethylene is reacted to form polyethylene, such as $CH_3(CH_2)_{500}CH_3$, for which the repeat unit is —$CH_2$—$CH_2$— and for which ethylene $CH_2\!\!=\!\!CH_2$ would be considered to be a monomer. Thus, the monomer may contain bonds, and/or atoms that are lost once the polymer is formed, and therefore the monomer and repeat unit are not identical, but are related. An "oligomer" is a compound of fewer than 20 repeat units, and as defined herein, is a subset of polymers. Polymers may be straight or branched chain, star-like or dendritic, or a polymer may be attached (grafted) onto another polymer. Polymers may be cross-linked to form a network.

As used herein, "copolymer" refers to a polymer which includes more than one type of repeat unit (or formed from a reaction of more than one type of monomer).

As used herein, a poly(ester-amide) refers to a polymer that has in its backbone structure both ester and amide bonds.

As used herein, a poly(amide) refers to a polymer that has in its backbone structure amide bonds.

As used herein, the terms "biodegradable," "bioerodable," and "bioabsorbable," as well as degraded, eroded, absorbed, and dissolved, when used in reference to polymers, coatings, coating layers, or other materials referenced herein, are used interchangeably, and refer to polymers, coatings, coating layers, and materials, that are capable of being completely, or substantially completely, degraded, dissolved, and/or eroded over time when exposed to physiological conditions (pH, temperature, and fluid or other environment), and can be gradually resorbed, absorbed and/or eliminated by the body, or that can be degraded into fragments that can pass through the kidney membrane of an animal (e.g., a human). Conversely, a "biostable" polymer, coating, coating layer, or material, refers to a polymer, coating, coating layer, or material that is not biodegradable.

As used herein, a material that is described as a layer or a film (e.g., a coating layer) "disposed over" an indicated substrate refers to, e.g., a coating layer of the material deposited directly or indirectly over at least a portion of the surface of the substrate. Direct depositing means that the coating layer is applied directly to the surface of the substrate. Indirect depositing means that the coating layer is applied to an intervening layer that has been deposited directly or indirectly over the substrate. A coating layer is supported by a surface of the substrate, whether the coating layer is deposited directly, or indirectly, onto the surface of the substrate. The terms "layer" and "coating layer" will be used interchangeably and refer to a layer, film, or coating layer as described in this paragraph. Unless the context clearly indicates otherwise, a reference to a layer or a coating layer refers to a layer of material that covers all, or substantially all, of the surface (for example, without limitation, all of the outer surface), whether deposited directly or indirectly. As used herein, the term "coating" refers to one or more layers deposited on a substrate as described in this paragraph. Thus, the term coating can refer to one or multiple layers.

As used herein, a "primer layer" refers to a coating layer consisting of one or more polymers, and/or other materials, that exhibit good adhesion characteristics with regard to the material of which the substrate is manufactured and good adhesion characteristic with regard to whatever material is to be coated on the substrate. Thus, a primer layer serves as an adhesive intermediary layer between a substrate and materials to be carried by the substrate and is, therefore, applied directly to the substrate. A non-limiting example of a substrate is a device body.

As used herein, "drug reservoir layer" refers to a layer of one or more polymers, optionally with other materials, that has dispersed within its three-dimensional structure, at least one peptide or protein and at least one hydrophobic drug. A polymeric drug reservoir layer is designed such that, by one mechanism or another, e.g., without limitation, by elution or as the result of biodegradation of the polymer, the drug is released from the layer into the surrounding environment. Other layers may optionally include a drug, but will not be referred to as a "drug reservoir layer" unless consistent with the definition above.

As used herein, "solvent" is defined as a substance capable of dissolving or dispersing one or more substances, or capable of at least partially dissolving and/or dispersing the substance(s), to form a uniform dispersion or solution at a selected temperature and pressure. A solvent can refer to one compound, or a mixture of compounds. A solvent can be a fluid.

As used herein, the term "solubility parameter," δ, refers to a parameter indicating the cohesive energy density of a substance. The δ parameter is determined as follows:

$$\delta = (\Delta E/V)^{1/2}$$

where δ is the solubility parameter, $(cal/cm^3)^{1/2}$;
ΔE is the energy of vaporization, cal/mole; and
V is the molar volume, $cm^3/mole$.

As used herein, "cumulative drug release" refers to the total amount of drug released from the drug delivery system or formulation up to a given point in time, such as, without limitation, 24 hours. The "cumulative drug release" is usually expressed as a percent of the total content (total drug content) of the drug delivery system or formulation. In such a calculation, the total content that is used in the denominator may be obtained from actual measurements (analytical assay of a number of units), theoretical (for example gravimetric weight gain after the application of a coating layer, and the calculation of the percent weight gain that is drug based upon the percent of solids in the coating solution or dispersion that is drug), label claim, or theoretical or objective drug loading. A non-limiting example of a drug delivery system is a stent coated with a drug reservoir layer.

As used herein, "substantially released," in reference to the release of a drug, refers to a cumulative release of the drug of about 80% or more.

As used herein, "sustained release" refers to a drug delivery profile in which the drug is released into the body over an extended period of time. The exact delivery profile is not limited. As two non-limiting examples, the drug may be released at a constant release rate (zero-order), or as a function of the square root of time (first order).

As used herein, any measurement of drug release, for example without limitation, release rate, cumulative release, or substantially released, refers to an in-vitro measurement of drug release utilizing scintillation vials (or another vial or container) that are shaken on an Orbit Environ Shaker (or substantially equivalent equipment) with porcine serum with optionally sodium azide added (such as, without limitation, at 0.3% w/v) at a temperature of 37° C. as the dissolution media. The coated substrate is submerged in scintillation vials containing 20 ml of Porcine Serum. At each time point, a number of coated substrates are removed and saved for extraction analysis, and the porcine serum solutions are discarded. The following parameters apply: agitation: 175 rpm; temperature: 37° C.; release medium: porcine serum (0.3% w/v sodium azide is optional); and media volume: 20 ml. The drugs remaining in the coating is determined by an appropriate assay such as, without limitation, HPLC. The volume of solution, the size of vial, and the time-points for removal of the substrate for later assay, may vary depending upon the coated substrate being tested.

The concentration of the drug in solution can be determined, for example, by an appropriate assay. Furthermore, the terms "drug release rate," "cumulative drug release," or the "drug is substantially released" will encompass release of a protein or peptide which has a therapeutic effect, or when the context clearly indicates inclusion of peptides and/or proteins.

Peptide or Protein

The various embodiments of the present invention encompass the delivery of at least one peptide or at least one protein from a drug reservoir layer. In the discussion that follows, although "a peptide or a protein" may be referred to, it is to be understood that the various coating layers which form embodiments of the invention are not limited to the inclusion of a single peptide or a single protein, but also encompass the inclusion of one peptide and one protein, one peptide and multiple proteins, multiple peptides and one protein, and multiple peptides and multiple proteins.

Encompassed in the various embodiments of the present invention are peptides and proteins that can be dissolved in ethanol at a sufficient concentration to be applied to a substrate as a coating layer, or as a component of a coating layer, and that are not denatured as a result of the dissolution in ethanol. Some embodiments of the present invention include those peptides or proteins that are soluble in ethanol, while other embodiments of the present invention include those peptides or proteins with limited solubility in ethanol.

Some embodiments of the present invention include a drug reservoir layer including a peptide of 2 to 8 amino acids, and more narrowly, 2 to 6 amino acids.

Embodiments of the present invention encompass the delivery of drugs (including proteins or peptide classified as drugs) that promote the attachment, migration or proliferation of endothelial cells (e.g., natriuretic peptides such as CNP, ANP or BNP peptide or an RGD or cRGD peptide), while impeding smooth muscle cell proliferation.

RGD is the polypeptide Arg-Gly-Asp (RGD) that has been demonstrated to be a bioactive factor for human endothelial cell attachment and therefore will be expected to exhibit prohealing characteristics. Prohealing refers to a substance that is biocompatible and that aids in the amelioration of inflammation, and/or promotes healing. The RGD (tri-peptide) sequence can be found in numerous proteins and extracellular matrix, as well as in short peptides whether they are linear, cyclic, free or linked. In addition to RGD itself, RGD peptide or cyclic RGD peptide (cRGD), synthetic cyclic RGD (cRGD) mimetics, and small molecules binding to other adhesion receptors differentially expressed on the endothelial cells, are within the scope of this invention. The cRGD or RGD mimetics described herein includes any peptides or peptide mimetics that result from the modification of the cyclic Arg-Gly-Asp peptide. The modification can be on the pendant groups and/or on the backbone of the peptide.

Peptide synthesis, including the synthesis of peptide mimetics, is well documented and can be readily achieved using, for example, combinatorial chemistry. Some examples of cRGD or RGD mimetics include $v_3$ antagonists such as glycoprotein IIb/IIIb antagonists (B. S. Coller, *Thromb. Haemost.* 2001, 86:427-443 (Review)), one example of which is Abciximax (R. Blindt, *J. Mol. Cell. Cardiol.* 2000, 32:2195-2206), XJ 735 (S. S. Srivastva et al., *Cardiovasc. Res.* 1997, 36:408-428), anti-$_3$-integrin antibody F11, cRGD (M. Sajid et al., *Am. J. Physiol. Cell Physiol.*, 2003, 285:C1330-1338), and other sequences such as laminin derived SIKVAV (M. H. Fittkau et al., *Biomaterials,* 2005, 26:167-174), laminin derived YIGSR (S. Kouvroukoglou et al., *Biomaterials,* 2000, 21:1725-1733), KQAGDV, and VAPG (B. K. Mann, B. K., *J. Biomed. Mater. Res.* 2002, 60:86-93).

The term "cRGD peptide" includes any proteins or peptides that comprise cRGD. The term "cRGD" can be used interchangeably with the term "RGD peptide." In those embodiments where the peptide or protein is a cRGD peptide, a RGD peptide, or a mimetic of either one, the drug load requirement in the coating layer may be the amount sufficient for recruiting endothelial progenitor cells.

Hydrophobic Drugs

The various embodiments of the present invention encompass a drug reservoir layer including at least one hydrophobic drug along with at least one protein or peptide as described above. Although the discussion that follows may make reference to "the hydrophobic drug" or "a hydrophobic drug," it is to be understood that the various embodiments of the present invention encompass drug reservoir layers including only one hydrophobic drug and including two or more hydrophobic drugs.

Some embodiments of the present invention include hydrophobic drugs that are soluble in ethanol at normal atmospheric pressure, and a temperature at which the coating process may be operated. A representative and non-limiting temperature range is 20° C. to 78° C. The solubility in ethanol may be sufficient to allow application of a coating to a substrate. Other embodiments include hydrophobic drugs with limited solubility in ethanol.

In some embodiments, the hydrophobic drug utilized may be one that is partially or completely, miscible, or soluble, in the polymer at the drug to polymer ratio utilized in the drug reservoir layer, where solubility or miscibility is determined at 20° C. In some embodiments, the hydrophobic drug utilized may be partially or completely miscible with a block of a block copolymer used in the coating layer. In some embodiments, the hydrophobic drug utilized is compatible with the polymer used in the drug reservoir layer.

Hydrophobic compounds typically have a low solubility parameter when compared to water. In some embodiments, a drug sufficiently hydrophobic to be solubilized, stabilized and used in accordance with the present invention may have a solubility parameter equal to or lower than about 11.5 (cal/cm$^3$).$^{1/2}$ In some embodiments, the hydrophobic drug utilized may be one that has a molecular weight in the range of 200 Da to 2000 Da, preferably 500 Da to 1500 Da, and more preferably 800 Da to 1100 Da.

One class of drugs that contains many hydrophobic drugs and which are particularly useful are anti-proliferative drugs. The term "anti-proliferative" as used herein, refers to a drug that works to block the proliferative phase of acute cellular rejection. Examples of anti-proliferative drugs include rapamycin (sirolimus) and its functional or structural derivatives including without limitation, Biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy] ethyl-rapamycin (a structural derivative of rapamycin), 40-O-tetrazole-rapamycin (a structural derivative of rapamycin), 40-O-tetrazolylrapamycin, 40-epi-(N1-tetrazole)-rapamycin, and the functional or structural derivatives of everolimus, paclitaxel and its functional and structural derivatives. Examples of paclitaxel derivatives include docetaxel. The anti-proliferatives described herein are generally hydrophobic.

Any drugs having anti-proliferative effects can be used in the present invention. The anti-proliferative drug can be a natural proteineous agent such as a cytotoxin or a synthetic molecule. Other active agents included in the various embodiments of the present invention include, without limitation, anti-proliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I$_1$, actinomycin X$_1$, and actinomycin C$_1$), all taxoids such as taxols, docetaxel, and paclitaxel, paclitaxel derivatives, all olimus drugs, FKBP-12 mediated mTOR inhibitors, and perfenidone, prodrugs thereof, co-drugs thereof, and combinations thereof.

Other potential drugs include, without limitation, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), dexamethasone, γ-hiridun, clobetasol, dexamethasone acetate, mometasone, imatinib mesylate, midostaurin, feno fibrate, feno fibric acid, and prodrugs thereof, co-drugs thereof, and combinations thereof.

Other Drugs

Drugs other than the at least one peptide or protein described above and the at least one hydrophobic drug described above may be included in the at least one drug reservoir layer as well as any other layer. Examples of suitable drugs, which may also be classified as hydrophobic drugs, include, but are not limited to, synthetic inorganic and organic compounds, proteins and peptides, polysaccharides and other sugars, lipids, and DNA and RNA nucleic acid sequences having therapeutic and/or prophylactic activities. Nucleic acid sequences include genes, antisense molecules that bind to complementary DNA to inhibit transcription, and ribozymes. Some other examples of other active agents include antibodies, receptor ligands such as the nuclear receptor ligands estradiol and the retinoids, enzymes, adhesion peptides, blood clotting factors, inhibitors or clot dissolving drugs such as streptokinase and tissue plasminogen activator, antigens for immunization, hormones and growth factors, oligonucleotides such as antisense oligonucleotides, ribozymes and retroviral vectors for use in gene therapy, and genetically engineered endothelial cells. Other drugs include heparin, fragments and derivatives of heparin, glycosamino glycan (GAG), GAG derivatives, alpha-interferon, and thiazolidinediones (glitazones). The active agents could be designed, e.g., to inhibit the activity of vascular smooth muscle cells. They could be directed at inhibiting abnormal or inappropriate migration and/or proliferation of smooth muscle cells to inhibit restenosis.

Examples of drugs that may be suitable for use in the various embodiments of the present invention, depending, of course, on the specific disease being treated, include, without limitation, anti-restenosis, pro- or anti-proliferative, anti-SF inflammatory, anti-neoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective drugs.

Anitproliferative drugs are outlined above.

Additional examples of cytostatic or antiproliferative drugs include, without limitation, angiopeptin, and fibroblast growth factor (FGF) antagonists.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro- fen, cintazone, cliprofen, clobetasol propionate, clobetasone butyrate, clopirac, cloticasone propionate, cormethasone acetate, cortodoxone, deflazacort, desonide, desoximetasone, dexamethasone, dexanethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Alternatively, the anti-inflammatory drug can be a biological inhibitor of pro-inflammatory signaling molecules. Anti-inflammatory bioactive agents include antibodies to such biological inflammatory signaling molecules.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of ACE inhibitors include, without limitation, quinapril, perindopril, ramipril, captopril, benazepril, trandolapril, fosinopril, lisinopril, moexipril and enalapril.

Examples of angiogensin II receptor antagonists include, without limitation, irbesartan and losartan.

Other drugs include anti-infectives such as antiviral drugs; analgesics and analgesic combinations; anorexics; antihelmintics; antiarthritics, antiasthmatic drugs; anticonvulsants; antidepressants; antidiuretic drugs; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing drugs.

Some drugs may fall into more than one of the above mentioned categories.

Polymers in Coating Layer

The various embodiments of the present invention utilize polymers that are biocompatible. The various embodiments of the present invention encompass blends of polymers as well as use of one type of polymer. The various embodiments of the present invention include the use of biodegradable, and/or biostable polymers in the drug reservoir layer. The various embodiments of the present invention encompass those polymers that may be used in a coating layer which provides for sustained release of both a hydrophobic drug and a hydrophilic peptide or protein. One such class of polymers is block copolymers that have a hydrophobic block and a hydrophilic block. For such polymers, the hydrophobic and hydrophilic blocks should be sufficiently long that the blocks may form separate domains within the coating layer.

Some embodiments of the present invention include those polymers with a molecular weight in the range of 10,000 to 250,000 Daltons, preferably 70,000 to 150,000 Daltons, and more preferably, 90,000 to 120,000 Daltons.

Some embodiments of the present invention include those polymers that are soluble in ethanol sufficiently to allow for application of a coating. Examples of such polymers, without limitation, are phosphorylcholine substituted polymers such as polyesteramides, polyacrylates, or polymethacrylates. Some embodiments include polymers soluble in another solvent in which both the hydrophobic drug and the protein and/or peptide of the drug reservoir layer are soluble.

The various embodiments of the present invention include the following list of polymers: poly(ester-amide) polymers, poly(amides), polymers soluble in ethanol, and phosphorylcholine substituted polymers such as polyesteramides, polyacrylates, or polymethacrylates. A specific non-limiting example of another polymer is a phosphorylcholine-linked methacrylate polymer, 1036 (PC-1036™ from Biocompatibles Ltd, Farnham, Surrey, United Kingdom), poly(2-(methacryloyloxyethyl)-2'-(trimethylammoniumethyl) phosphate, inner salt)-co-(dodecyl methacrylate)-co-(2-hydroxypropylmethacrylate)-co-(3-Trimethoxysilyl) propylmethacrylate (23:47:25:5 mole %), which is a random copolymer of four components. The structure of PC-1036 is the following:

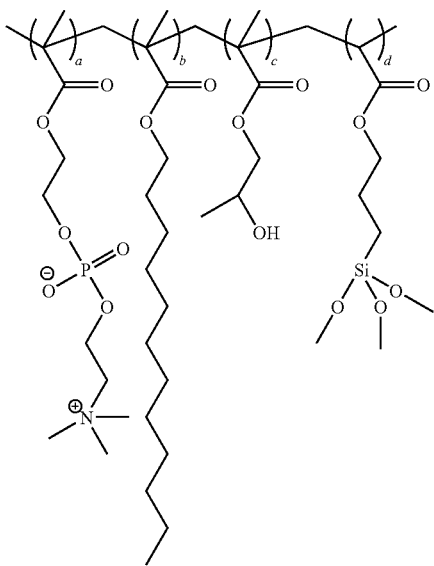

In the above illustration, a, b, c, and d stand for the stoichiometric (theoretical) ratios of each monomer. There are multiple monomers in the polymer.

Embodiments of the present invention encompass those polymers that are miscible with the hydrophobic drug of the coating layer, partially miscible or partially soluble, completely miscible, or substantially completely miscible, at the drug to polymer ratio utilized in the drug reservoir layer. In some embodiments utilizing a block co-polymer, the hydrophobic drug may be miscible with one of the blocks of the copolymer which forms one or more domains in the coating layer. In some embodiments, the polymer is one with which the hydrophobic drug is compatible. In some embodiments, the polymer utilized may have a solubility parameter within 1.5 $(cal/cm^3)^{1/2}$ of the hydrophobic drug used in the coating layer (where an average solubility parameter based on mass % is used if there is more than one polymer). In some embodiments, the polymer utilized may be a block copolymer with a polymer block having a solubility parameter within 1.5 $(cal/cm^3)^{1/2}$ of the hydrophobic drug used in the coating layer. In some embodiments using a block copolymer, there may not be any limitations on the value of the solubility parameter of the other block.

Some embodiments of the present invention include those polymers with a glass transition temperature in the range of −20° C. to 100° C., preferably 30° C. to 90° C. and more preferably, 45° C. to 65° C.

Other polymers that may be utilized include poly(ester-amide) and poly(amide) polymers. Poly(ester-amide) and poly(amide) polymers that may be used in the various embodiments of this invention have the generic formula:

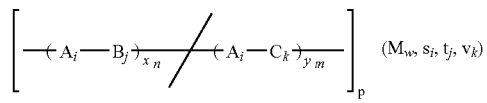

wherein the constitutional units are represented by $A_i$-$B_j$ and $A_i$-$C_k$ where the $A_i$ and $B_j$ react to form the constitutional unit represented by $A_i$-$B_j$ and $A_i$ and $C_k$ react to form the constitutional unit represented by $A_i$-$C_k$. The $A_i$ groups are derived from diacids, and the $B_j$ groups are derived from diamino esters. The group $C_k$ is a lysine group. Thus, each $A_i$ has the chemical structure:

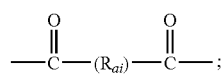

each $B_j$ has the chemical structure

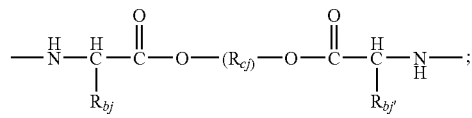

and each $C_k$ has the chemical structure:

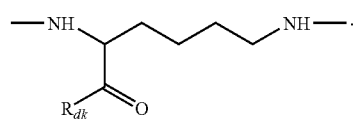

As noted above, the constitutional units themselves may be the product of the reactions of other compounds. For example, without limitation, a $B_j$ group above can comprise the reaction of an amino acid,

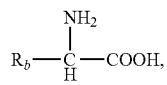

with a diol, HO—($R_c$)—OH, to give a diamino ester,

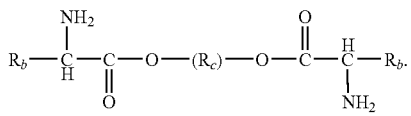

The diamino ester may be further reacted with a diacid,

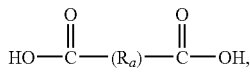

to give the constitutional unit, represented by $A_i$-$B_j$. The amine group, the carboxylic acid group or the hydroxyl group may be "activated," i.e., rendered more chemically reactive, to facilitate the reactions if desired; such activating techniques are well-known in the art and the use of any such techniques is within the scope of this invention.

While any amino acid may be used to construct a poly (ester-amide) of this invention, particularly useful amino acids are the so-called essential amino acids of which there are currently 20: alanine, arginine, asparagine, aspartic acid, cysteine, glutamic acid, glutamine, glycine, histidine, isoleucine, leucine, lysine, methionine, phenyl alanine, proline, serine, threonine, tryptophan, tyrosine and valine. More recently selenoadenine has been found to be incorporated into a number of proteins and is included as a particularly useful amino acid of this invention. In naturally-occurring biological proteins, these amino acids appear as the l-enantiomeric isomers but for the purposes of this invention they may be used as their l- or d-enantiomers or as racemic mixtures.

On the lysine unit, represented by $C_k$, the $R_{dk}$ can be a drug, a peptide (which may a drug or a targeting moiety), a polymer, an oligomer, or another type of functional group. The polymer or oligomer may be hydrophilic or hydrophobic. $R_{dk}$ may also be a protective group to prevent the pendent acid functionality from participating in the polymerization reaction.

The linkage used to directly attach $R_{dk}$ to the carbonyl of the lysine may be an ester, a thioester, an amide, an anhydride, or an imide or $R_{dk}$ may be connected to the carbonyl through a spacer such as, without limitation, a C1-C12 alkyl or a poly(alkylene oxide) such as poly(ethylene glycol) or poly (propylene oxide).

As noted above, each $A_i$ and $B_j$ represents one or more different groups derived from diacids or derived from diamino esters, respectively, which may react to form the constitutional units, where i represents the $i^{th}$ type of $A_i$ group, j represents the $j^{th}$ type of $B_j$ group, and k represents the $k^{th}$ type of $C_k$ groups. Each polymer may have from 1 to 10 $A_i$ groups. Similarly, each polymer may have from 0 to 10 $B_j$ groups, and from 0 to 15 $C_k$ groups. A particular polymer may have fewer than the maximum, or 10, different $A_i$ groups. Thus if i=3, there is an $A_1$, $A_2$ and $A_3$ group. Similarly a particular polymer may have fewer different $B_j$ groups than the maximum, 10, and a particular polymer may have less than the maximum number of types of $C_k$ groups possible, that is 15. Therefore, if j=2, there is a $B_1$ and a $B_2$ group, and if k=0 there are no $C_k$ groups. There must be at least one $A_i$ group, or i is at least one (1). In addition, there must be at least one $B_j$ group, or at least one $C_k$ group, or in other words, both j and k cannot equal zero (0).

The subscripts $x_n$ and $y_m$ are integers which represent the number of different possible types of $A_i$-$B_j$ and $A_i$-$C_k$ constitutional units in a polymer chain, respectively, and p is an integer which represents the average total number of constitutional units in an average polymer chain. Thus, each $x_n$ is an integer from about 0 to about 100, and $y_m$ is an integer from about 0 to 150, subject to the constraint that at least one $x_n$ or at least one $y_m$ is non-zero. The number of different $x_n$ groups is a function of the number of different $A_i$ groups and different $B_j$ groups as there is an $x_n$ for each $A_i$-$B_j$ group. For example if there are two $A_i$ groups and three $B_j$ groups, there will be six possible $A_i$-$B_j$ groups ($A_1$-$B_1$, $A_1$-$B_2$, $A_1$-$B_3$, $A_2$-$B_1$, $A_2$-$B_2$, $A_2$-$B_3$), and six $x_n$'s ($x_1$, $x_2$, $x_3$, $x_4$, $x_5$, $x_6$). The number of different $y_m$ groups is a function of the number of different $A_i$ groups and different $C_k$ groups as there is an $y_m$ for each $A_i$-$C_k$ group. For example, if there are two $A_i$ groups and three $C_k$ groups, there will be six possible $A_i$-$C_k$ groups ($A_1$-$C_1$, $A_1$-$C_2$, $A_1$-$C_3$, $A_2$-$C_1$, $A_2$-$C_2$, $A_2$-$C_3$), and six $y_m$'s ($y_1$, $y_2$, $y_3$, $y_4$, $y_5$, $y_6$). The average number of constitutional units in a chain, p, is an integer from 2 to about 4500.

Also in the above formula, each of the $s_i$, $t_j$, and $v_k$ represent the average mole fraction of each of the $A_i$, $B_j$, and $C_k$, respectively, which react to form the constitutional units. Each of the $s_i$, $t_j$, and $v_k$ is a number between 0 and 0.5, inclusive and subject to the constraints that $\Sigma_i s_i + \Sigma_j t_j + \Sigma_k v_k = 1.0$, and $\Sigma_i s_i = \Sigma_j t_j + \Sigma_k v_k = 0.5$ where each summation of $s_1$ is from 1 to the number of different $A_i$ groups (maximum of 10), each summation of $t_j$ is from 0 to the number of different $B_j$ groups (maximum of 10), and each summation of $v_k$ is from 0 to the number of different types of $C_k$ groups (maximum of 15). The values are also subject to the limitations that $\Sigma_i s_i > 0$, and either $\Sigma_j t_j > 0$ or $\Sigma_k v_k > 0$, or there is at least one non-zero $s_i$ along with at least one $t_j$ or at least one $v_k$ which is non-zero. Thus, in some embodiments, all $v_k$ may be 0, or $\Sigma_k v_k = 0$, or all $t_j$ may be 0 or $\Sigma_j t_j = 0$, but there are no embodiments where both $\Sigma_k v_k = 0$, and $\Sigma_j t_j = 0$. The mole fraction and the number of constitutional units are obviously related and it is understood that the designation of one will affect the other.

Other than the preceding provisos, $s_i$, $t_j$, and $v_k$ may be any mole fractions that provide a polymer that exhibits desirable properties for the particular use it is to put as set forth here, e.g., as part of a coating for an implantable medical device, subject to the limitations outlined above. However preferred values of $v_k$ are about 0.1 or less if the $C_k$ group is reacted as a free acid ($R_{dk}$="H" or hydrogen). Furthermore, it is preferred that the value of $v_k$ may be low for use with a more hydrophobic drug. Those of ordinary skill in the art will be able to manipulate the mole fractions, prepare the polymers and examine their properties to make the necessary determination based on the disclosures herein without resorting to undue experimentation.

In some embodiments, the polymers may be subject to the proviso that at least one $R_{ai}$ or at least one $R_{cj}$ is selected from the group consisting of

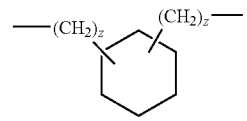

where z is 0, 1, or 2. The $R_{ai}$ is part of the $A_i$ group, and the $R_{cj}$ is part of the $B_j$ group. Thus, in those embodiments in which j=0 (or $\Sigma_j t_j = 0$), at least one $R_{ai}$ must be selected from the group outlined above.

The polymer represented by the above formula may be a random, alternating, random block or alternating block polymer. The term "–/–" means that the $A_i$-$B_j$ group may be attached to or reacted with another $A_i$-$B_j$ group, either including the same $A_i$ and $B_j$ or at least one of the $A_i$ and $B_j$ differ, or alternatively, a $A_i$-$C_k$ group. Thus the generic formula encompasses the following exemplary embodiments without limitation. In an exemplary but non-limiting embodiment, if the number of $A_i$ groups is 2 and the number of $B_j$ groups is 2, and the number of $C_k$ groups is 1, the following types of polymers are encompassed by the generic formula:

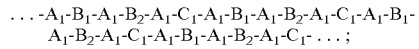   1)

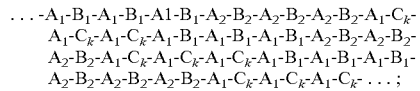   2)

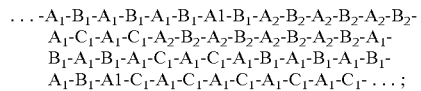   3)

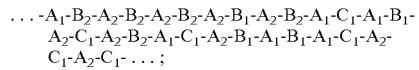   4)

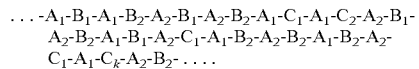   5)

Thus, there are six potential constitutional units, $A_1$-$B_1$, $A_1$-$B_2$, $A_2$-$B_1$, $A_2$-$B_2$, $A_1$-$C_1$, and $A_2$-$C_2$. As the exemplary embodiments above illustrate, the polymer may be a completely random polymer, a regular alternating polymer, a random alternating polymer, a regular block polymer, or a random block polymer. As illustrated in polymer (2) above, only three groups are included $A_1$-$B_1$, $A_2$-$B_2$, and $A_1$-$C_1$. Such a polymer may be manufactured by reacting the separate blocks and then combining the blocks. Other polymers encompassed by the generic formula contain all six possible constitutional units, such as polymers (4) and (5).

Thus, the generic formula encompasses a polymer with only one type of constitutional unit. If there is only one $A_i$ and only one $B_j$ and no $C_k$ groups, there is only the $A_1$-$B_1$ unit. If there is only one $A_i$ and no $B_j$ groups and only one $C_k$ group, then there is only the $A_1$-$C_1$ unit. If there is only one $A_i$, only one $B_j$ and only one $C_k$ group, or only one $A_i$, only two $B_j$ groups, and not any $C_k$ groups, or two $A_i$ groups, and either only one $B_j$ group and not any $C_k$ groups, or only one $C_k$ group, and not any $B_j$ groups, there will be two potential constitutional units -$A_1$-$B_1$ and $A_1$-$C_1$ units, $A_1$-$B_1$ and $A_1$-$B_2$ units, $A_1$-$B_1$ and $A_2$-$B_1$ units, or $A_1$-$C_1$ and $A_2$-$C_1$ units, respectively. In general, the total number of potential constitutional units will be equal to the sum of the number of different types of $A_i$ groups times the number of different types of $B_j$ groups, plus the number of different types of $A_i$ groups times the number of different types of $C_k$ groups. As outlined above, not all potential constitutional units may be included in each embodiment.

In the above formula, $M_w$ represents the weight average molecular weight of the polymer of this invention. Again, while any molecular weight that results in a polymer that has the requisite properties to be used in a coating, at present the weight average molecular weight of a polymer of this invention is from about 10,000 Da (Daltons) to about 250,000 Da.

With regard to the synthesis of the polymers of this invention, it will be noted that no specific reactions or reaction conditions are exemplified herein. This is because the reactions and reaction conditions both for the preparation of constitutional units and for the preparation of the final polymer are standard organic and organic polymer chemistry well-known to those of ordinary skill in the art and, therefore, those skilled artisan would be able to prepare any of the compounds herein without undue experimentation based on the disclosures herein. However, when utilizing the $C_k$ at a level greater than about 10%, the $C_k$ group should not be reacted as a free acid but should include an $R_{dk}$ protective group. In other words, if $C_k$ is the free acid, then $v_k \leq 0.1$. In some embodiments, the $R_{dk}$ group will be altered after the polymerization reaction.

As used herein, "alkyl" refers to a straight or branched chain fully saturated (no double or triple bonds) hydrocarbon (carbon and hydrogen only) group. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl. As used herein, "alkyl" includes "alkylene" groups, which refer to straight or branched fully saturated hydrocarbon groups having two rather than one open valences for bonding to other groups. Examples of alkylene groups include, but are not limited to methylene, —$CH_2$—, ethylene, —$CH_2CH_2$—, propylene, —$CH_2CH_2CH_2$—, n-butylene, —$CH_2CH_2CH_2CH_2$—, sec-butylene, —$CH_2CH_2CH(CH_3)$— and the like.

As used herein, "Cm to Cn," wherein m and n are integers refers to the number of possible carbon atoms in the indicated group. That is, the group can contain from "m" to "n", inclusive, carbon atoms. An alkyl group of this invention may comprise from 1 to 20 carbon atoms that is m may be 1 and n may be 20. The alkyl group may be linear, branched, or cyclic. Of course, a particular alkyl group may be more limited, for instance without limitation, to 3 to 8 carbon atoms, in which case it would be designate as a (C3-C8)alkyl group. The numbers are inclusive and incorporate all straight or branched chain structures having the indicated number of carbon atoms. For example without limitation, a "C1 to C4 alkyl" group refers to all alkyl groups having from 1 to 4 carbons, that is, $CH_3$—, $CH_3CH_2$—, $CH_3CH_2CH_2$—, $CH_3CH$($CH_3$)—, $CH_3CH_2CH_2CH_2$—, $CH_3CH_2CH(CH_3)$— and ($CH_3$)$_3$CH—.

As use herein, a "cycloalkyl" group refers to an alkyl group in which the end carbon atoms of the alkyl chain are covalently bonded to one another. The numbers "m" to "n" then refer to the number of carbon atoms in the ring so formed. Thus for instance, a (C3-C8)cycloalkyl group refers to a three, four, five, six, seven or eight member ring, that is, cyclopropane, cyclobutane, cyclopentane, cyclohexane, cycloheptane and cyclooctane.

As used herein,

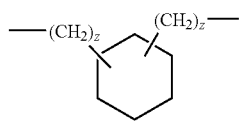

represents a cyclohexane group, optionally with a —$CH_2$— or a —$CH_2$—$CH_2$— group attached at any two locations on the ring, which is the optional groups may be attached at the 1 & 2, 1 & 3, or 1 & 4 positions. Alternatively, if z=0, the ring may attach to the other atoms in the molecule at the 1 & 2, 1 & 3, or 1 & 4 positions. Thus the following structures are encompassed:

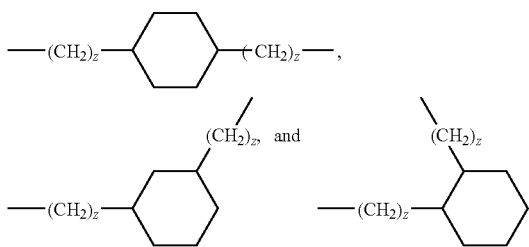

where z is 0, 1, or 2. The conformation of the cyclohexyl groups may be any of the potential conformations which are chair, half-chair, twist boat, or boat. The substituent groups, or the bonds with other molecules, may be either cis or trans.

As used herein, "alkenyl" refers to an alkyl group that contains one or more double bonds.

As used herein, "alkynl" refers to an alkyl group that contains one or more triple bonds.

Standard shorthand designations well-known to those skilled in the art are used throughout this application. Thus the intended structure will easily be recognizable to those skilled in the art based on the required valency of any particular atom with the understanding that all necessary hydrogen atoms are provided. For example, —COR, because carbon is tetravalent, must refer to the structure

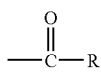

as that is the only way the carbon can be tetravalent without the addition of unshown hydrogen or other atoms.

Likewise, —O(CH)$_2$OP(—O)(O$^-$)OCH$_2$CH$_2$N$^+$(CH$_3$)$_3$ refers to the structure

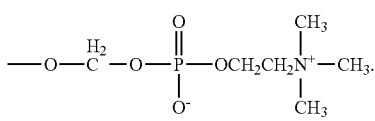

Other such designations will be readily interpretable by those skilled in the art based on the discussion herein.

With regard to the poly(ester-amide) and poly(amide) polymers of the present invention, the substituent groups may be chosen to provide for drug miscibility, drug solubility, and/or drug compatibility. For example the choice of an R$_{bj}$ group which is more hydrophobic and larger may increase the hydrophobicity of the polymer. The choice of a R$_{cj}$ or R$_{ai}$ group with bonds allowing for free rotation may decrease the glass transition temperature while a group with bonds that do not rotate as easily may increase the glass transition temperature. Similarly, the choice of a more or less hydrophobic group for R$_{cj}$ or R$_{ai}$ may change the hydrophobicity of the polymer. As noted above, the amide bond allows for hydrogen bonding with some drugs and in particular, some peptides and proteins.

Some embodiments of the present invention include poly (ester-amide) random copolymers of two constitutional units, A$_1$-B$_1$ and A$_1$-B$_2$, in which s1 is about 0.5, and t$_1$ is between 0.125 and 0.375, and t$_2$ is 0.5–t$_1$, and p is an integer from 2 to about 4500. Thus x=2, or there is an x$_1$ and an x$_2$ group, and y=0. R$_{a1}$ of group is A$_1$ is selected from the group consisting of —(CH$_2$)$_6$—, —(CH$_2$)$_7$—, —(CH$_2$)$_8$—, CH$_2$)$_9$—, and —(CH$_2$)$_{10}$—, R$_{b1}$, R$_{b1'}$, R$_{b2}$ and R$_{b2'}$ are all the same, and are selected from the group consisting of —(CH$_2$)—(CH(CH$_3$)$_2$) and —(CH$_3$), R$_{c1}$ is selected from the group consisting of —(CH$_2$)$_4$—, —(CH$_2$)$_5$—, —(CH$_2$)$_6$—, —(CH$_2$)$_7$—, and —(CH$_2$)$_8$—, and R$_{c2}$ is selected from the group consisting of

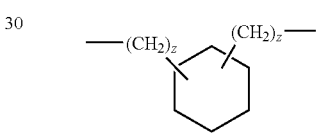

where z is 0, 1, or 2. In some embodiments, R$_{c2}$ is selected from

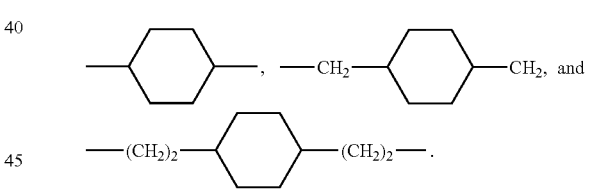

Some embodiments of the present invention include a poly (ester-amide) polymer which is a random co-polymer of the following formula [-(A$_1$-B$_1$)–/–(A$_1$-B$_2$)-]$_p$(M$_w$, r$_1$, r$_2$):

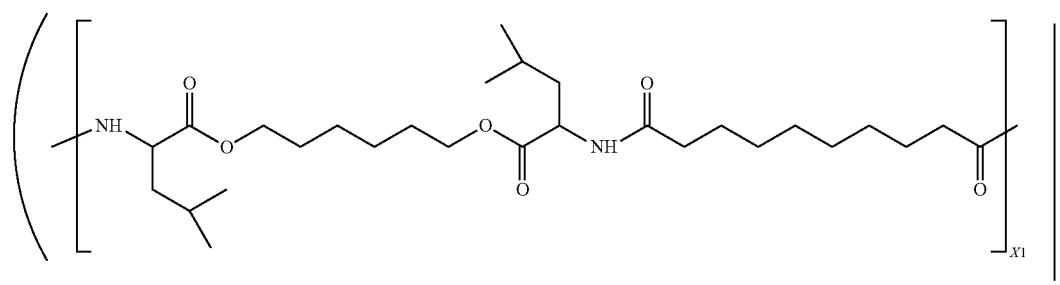

-continued

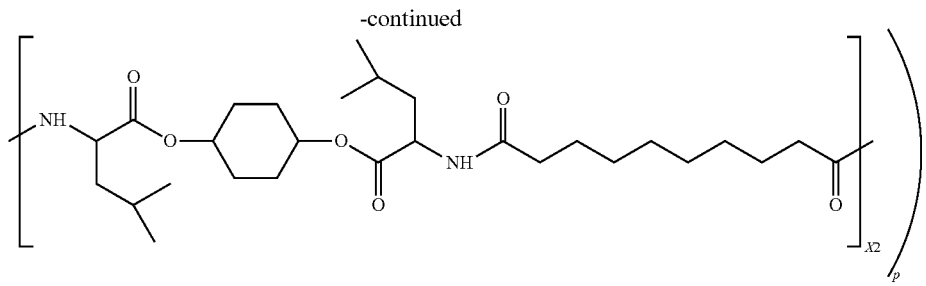

in which $A_1$ is 0.5, and each of $B_1$ and $B_2$ are about 0.25, and thus the mole fractions of the two constitutional units, X1 and X2, are each about 0.5, and p is the total number of X1 and X2 units on average, per polymer chain and ranges from 2 to about 4500. The two groups do not necessarily alternate regularly as this is a random copolymer, and there are multiple X1 and X2 groups per polymer chain. There may be large variations in the length of the polymer chains.

The polymers utilized in the various embodiments of this invention, whether poly(ester amide) polymers or other polymers, may be regular alternating polymers, random alternating polymers, regular block polymers, random block polymers or purely random polymers unless expressly noted otherwise. A representative polymer of x, y, and z constitutional units will be used to illustrate the various types of polymers. To illustrate, a regular alternating polymer has the general structure: . . . x-y-z-x-y-z-x-y-z- . . . . To illustrate, a random alternating polymer has the general structure: . . . x-y-x-z-x-y-z-y-z-x-y- . . . , it being understood that the exact juxtaposition of the various constitution units may vary. To illustrate further, a regular block polymer has the general structure: . . . x-x-x-y-y-y-z-z-z-x-x-x . . . , while an illustrative example of a random block polymer has the general structure: . . . x-x-x-z-z-x-x-y-y-y-y-z-z-z-x-x-z-z-z- . . . . Similarly to the situation above regarding regular and alternating polymers, the juxtaposition of blocks, the number of constitutional units in each block and the number of blocks in block polymers of this invention are not in any manner limited by the preceding illustrative generic structures.

Other biocompatible polymers that can be utilized to form a coating with the hydrophilic peptide or protein and the hydrophobic drug described herein. The biocompatible polymer can be biodegradable or nondegradable, and can be hydrophilic or hydrophobic.

Representative biocompatible polymers include, but are not limited to, poly(ester-amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), copolymers of any combination of the group consisting of D-lactic acid, L-lactic acid, D,L lactic acid, glycolic acid, and caprolactone, poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, (such as without limitation Nylon 66 and polycaprolactam), alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, other cellulose derivatives, polyethers, poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomer such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomer such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol block co-polymers), poly(tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, polysaccharide, chitosan, alginate, or combinations thereof.

As used herein, the terms poly(D,L-lactide), poly(L-lactide), poly(D,L-lactide-co-glycolide), and poly(L-lactide-coglycolide) can be used interchangeably with the terms poly(D,L-lactic acid), poly(L-lactic acid), poly(D,L-lactic acid-co-glycolic acid), or poly(L-lactic acid-co-glycolic acid), respectively.

Release Profiles

Various embodiments of the present invention encompass a drug reservoir layer to deliver both a peptide or protein and a hydrophobic drug. It has been found, surprisingly, that sustained release of both a hydrophobic drug and a peptide or protein could be obtained from a single coating layer. The sustained release of both a hydrophobic drug and a peptide or protein is obtained by the appropriate choice of polymer, drug to polymer ratio, ratio of protein or peptide to hydrophobic drug, and coating layer thickness.

The polymer chosen for forming the coating for controlled release of a peptide or protein and a hydrophobic drug should be compatible with both. Moreover, polymers in which the hydrophobic drug is at least partially miscible, or in other words, polymers in which the drug may be soluble to some extent, may be particularly suitable. Other important characteristics of the polymer include the mechanical properties and the film-forming properties. The polymer may be biocompatible, but are not necessarily biodegradable. Polymer blends may be used as well as combinations of biodegradable and biostable polymers. In some embodiments, other non-polymeric materials such as fillers, binders, carriers, plasticizers, and other additives may optionally be included in the drug reservoir layer.

Controlled release of both drugs (the peptide or protein and the hydrophobic drug) is also impacted by the drug to polymer ratio, as well as the ratio of the two drugs to each other. The choice of a higher amount of polymer generally results in a slower release, while too small an amount may lead to a too rapid release of one or both drugs. Furthermore, polymer content impacts the physical and mechanical integrity of the coating layer. As peptide and proteins are hydrophilic, the quantity of these drugs in the coating layer impacts the release of the one or more hydrophobic drugs, particularly if the one or more peptides and proteins are quickly released, leaving pores through which the one or more hydrophobic drugs may diffuse out. Thus, in some embodiments the mass ratio of at least one of the peptides or proteins to at least one of the hydrophobic drugs may be in the range of about 1:0.1 to about 1:10, preferably about 1:0.2 to about 1:5. In some embodiments, the ratio may be in the range of about 0.2:1 to 2:1. In some embodiments the mass ratio of the sum of all of the peptides or proteins to all of the hydrophobic drugs in a given drug reservoir layer may be in the range of about 1:0.1 to about 1:10, preferably about 1:0.2 to about 1:5. In some embodiments, the range may be from about 1:2 to 1:4. In some embodiments the mass ratio may be set by the desired dose of each drug to be administered. In some embodiments the ratio of at least one peptide or protein to at least one of the hydrophobic drugs may be about 1:1, or 1:1, while in some embodiments the ratio of at all of the peptides or proteins to all of the hydrophobic drugs may be about 1:1, or 1:1.

Various embodiments of the present invention encompass variations in the drug to polymer ratio. In some embodiments, the ratio of the peptide or protein to the ratio of polymer may vary from about 1:0.1 to about 1:10, preferably about 1:0.2 to about 1:5. In some embodiments, the ratio is about 1:0.5 to 3:1.

The thickness of the layer is also a parameter that impacts the release of the drugs. Thus, in some embodiments the coating layer thickness may be in the range of about 0.5 and about 9 μm, preferably about 0.5 and about 7 μm, and more preferably about 2 and about 7 μm.

The various embodiments of the present invention encompass drug reservoir layers for which the release of at least one peptide or protein and the release of at least one hydrophobic drug overlap, at least partially, in time. In some embodiments, the cumulative release of the peptide or protein may range from about 5% to about 50% at 24 hours, and from about 10% to about 95% at 7 days. In other embodiments, the cumulative release of the peptide or protein may range from about 8% to about 25% at 24 hours, and from about 10% to about 40% at 7 days. In some embodiments, the cumulative release of the hydrophobic drug may range from about 5% to about 50% at 24 hours, and from about 10% to about 95% at 7 days. In some embodiments, the cumulative release of the hydrophobic drug may range from about 10% to about 35% at 24 hours, and from about 25% to about 75% at 7 days.

In some embodiments, the hydrophobic drug may be substantially released at a time when the cumulative release of the protein or peptide is less than about 80%, while in other embodiments, the peptide or protein may be substantially released at a time when the cumulative release of the hydrophobic drug is less than about 80%. In some embodiments, there may be a delay in the release of the protein or peptide, followed by sustained release of the protein or peptide. In some embodiments, there may be a delay in the release of the hydrophobic drug followed by a sustained release of the hydrophobic drug. In some embodiments in which the release of either of the drugs is delayed, there may be some overlap in the release profiles.

Coating Constructs

In some embodiments, a coating layer provides for the sustained release of both a hydrophilic peptide or protein, and a hydrophobic drug (e.g., an anti-proliferative drug, such as, without limitation, everolimus), and this layer is referred to herein as a drug reservoir layer. In some embodiments, the coating on the implantable medical device, such as a stent, may contain only one layer that is the drug reservoir layer. The drug reservoir layer includes at least one hydrophobic drug and at least one protein or at least one peptide, although multiple hydrophobic drugs, or multiple members of the group consisting of peptides and proteins are also encompassed as outlined above.

In some embodiments, a primer layer may be deposited on the device prior to the application of the drug reservoir layer. The primer layer may include a polymer or material such as, without limitation, silanes, titanates, zirconates, silicates, parylene, polyacrylates and polymethacrylates, with poly(n-butyl methacrylate) being a presently preferred primer. There may be any number of coating layers between the primer layer and the drug reservoir layer.

In some embodiments there may be one or more additional layers above the drug reservoir layer. The additional one or more layers above the drug reservoir layer may be free of drugs, or this layer may include the hydrophilic peptide(s) and/or protein(s), and/or the hydrophobic drug(s) of the drug reservoir layer below. In some embodiments, additional layers may include at least one of the peptide(s) and/or protein(s) included in drug reservoir layer, but not any of the one or more hydrophobic drugs of the drug reservoir layer. These one or more additional layers may be designed to release the drug (protein and/or peptide) quickly, either as a result of choosing a polymer or material in which the peptide and/or protein is highly permeable, or choosing a polymer or material which readily dissolves under physiological conditions. A quick drug release may be defined as a drug release profile in which the drug is substantially released in less than about 48 hours, about 24 hours, about 12 hours, or about 6 hours. In some embodiments, at least one of the proteins or peptides may be released from an additional layer according to a sustained release profile. The release rate profile of the peptides or protein, such as without limitation a cRGD peptide, with a dose provided in a layer above the drug reservoir layer which quickly releases (sometimes referred to as a loading dose) may match the mechanistic temporal need for activation of EPC capture process. As noted previously, cRGD is a hydrophilic chemo-attractant for endothelial progenitor cells (EPCs). The long term release of the peptide or protein, such as, without limitation, a cRGD peptide, at low doses can maintain the recruiting of EPCs and continue to affect the surrounding endothelial cells and smooth muscle cells.

In other embodiments, one or more additional layers may include only one or more of the at least one hydrophobic drugs (and not any of the proteins or peptides of the drug reservoir layer), and the delivery profile may be a sustained release profile, or the one or more drugs may be quickly released. A quick drug release is defined above. In still other embodiments, the layer above the drug reservoir layer may be free of drug as applied, but the hydrophobic drug may partition or diffuse into the layer above the drug reservoir layer over time. The partitioning of the hydrophobic drug into the layer above the drug reservoir layer, may effectively provide a loading dose of the hydrophobic drug which is substantially released before the hydrophobic drug from the drug reservoir layer has been substantially released. In some embodiments, there may be multiple layers with or without a drug above the drug reservoir layer.

In any of the embodiments, any of the layers, including the optional primer layer, the drug reservoir layer, any optional layers above the drug reservoir layer, and any optional layers intervening between the primer layer and the drug reservoir layer may optionally include one or more drugs other than the one or more hydrophobic drugs and one or more peptides and/or proteins of the drug reservoir layer. Additionally, the hydrophobic drug(s) and/or the peptide(s) and/or protein(s) of the drug reservoir may also be included in any layer in addition to inclusion in the drug reservoir layer, but if both a hydrophobic drug and at least one of a protein or a peptide are included in a layer it would be referred to as a drug reservoir layer.

In some embodiments, there may be more than one drug reservoir layer that is a coating layer as defined above. In those cases, there may be any number of layers between the drug reservoir layers. In some embodiments, the multiple (two or more) drug reservoir layers may include the same drugs, that is the same one or more hydrophobic drugs and the same protein(s) and/or peptide(s). In some embodiments of multiple drug reservoir layers, at least one of the one or more hydrophobic drugs, or at least one peptide or protein, may be included in more than one drug reservoir layer. In some embodiments, the multiple drug reservoir layers may not include any drugs in common. In some embodiments, some drugs may be included in more than one drug reservoir layer, while other drugs may be included in only one drug reservoir layer.

The coating layers of these embodiments can be applied to any medical devices where the release of a hydrophobic drug and a peptide or protein from a single coating layer is necessary or desirable. Particularly suitable medical devices are implantable medical devices. A preferred device for use with the various embodiments of the present invention is a stent.

How to Make

There are a number of methods to apply a coating layer to a substrate including spray-coating, dipping, electrostatic coating, and ion beam deposition. However, the preferred method for the application of the coating layers of the present invention is via application of a solution or dispersion of the drugs, polymer, and optional other materials such as a polymer or polymers, that constitute the drug reservoir layer. Each layer of a coating on a medical device, such as a stent, can be disposed over the device by dissolving or dispersing the polymer, optionally with other additives, in a solvent, and disposing the resulting coating solution (or dispersion) over the device by procedures such as spraying or immersing the device in the solution (or dispersion). Spraying also generally involves atomization of the solution or dispersion by use of compressed air (or another compressed gas, or use of a supercritical fluid). To incorporate a drug into the coating layer, the drug can be combined with the polymer solution or dispersion. Such coating procedures are well-known in the art.

After the solution (or dispersion) has been disposed over the stent, the solvent is removed, or substantially removed, by evaporation. When the solvent is removed, what is left is the solid material which forms a layer, film, or coating layer on the surface of the implantable medical device, either directly or indirectly. The process of drying can be accelerated if the drying is conducted at an elevated temperature, and/or with the addition of a flow of air (or the flow of another gas, or the flow of a supercritical fluid), over or past the device to enhance mass transfer of the solvent. The coating layer left may include residual solvents as removal of absolutely all of the solvent is generally not possible.

The material dissolved or dispersed in the solvent to form a coating solution (or dispersion) and which remains after the solvent is evaporated may be referred to as the "solids content" in the solution or dispersion. For example if a solution (or dispersion) contains 4 weight % polymer and the remaining weight is solvent, the solution is said to have a 4% solids content. Thus, the drug loading in a coating layer may be determined by multiplying the weight gain resulting from the application of the coating layer by the weight % drug as a weight % solids in the solution, or in other words, the mass of drug added to the coating solution divided by the total mass of all solids (non-solvents) in the coating solution. In such calculations, the residual solvent content of the coating layer thus applied is generally ignored.

The coated medical device (such as a stent) may be optionally annealed at a temperature between about 40° C. and about 150° C. for a period of time between about 5 minutes and about 180 minutes, if desired, to allow solvent evaporation, for crystallization of the polymer in the coating, and/or to improve the thermodynamic long term stability of the coating.

In some embodiments, the coating may be applied by dissolving the at least one hydrophilic peptide or protein, the at least one hydrophobic drug, and the at least one polymer, and optional other materials in ethanol, and spraying the resulting coating solution (or dispersion) onto an implantable medical device. Spraying is performed in multiple passes and utilizes compressed air (or another compressed gas or a supercritical fluid) to atomize the solution (or dispersion). Application from ethanol allows for the removal of all, or substantially all, of the solvent at moderately low temperatures, such as without limitation, 50° C. The protein or peptide is not denatured by high temperatures, and the drug is not exposed to high temperatures which may result in drug degradation. Also, dissolving the protein or peptide in ethanol does not denature the protein or peptide. Moreover, ethanol is less toxic than many other solvents, and as a result, the residual solvent requirements are less stringent. The higher residual solvent levels also decrease the time frame of exposure to elevated temperatures for solvent removal. Thus, application of the coating layer from an ethanol solution (or dispersion) is one of the preferred embodiments. A preferred grade of ethanol is absolute ethanol, anhydrous, 99.5+ (ACS grade, CAS 64-17-5).

Method of Use

In accordance with embodiments of the invention, the coating layer according to the present invention can be included in an implantable device or prosthesis, e.g., a stent. For a device including one or more drugs, the drugs will be retained on the device such as a stent during delivery and expansion of the device, and released at a desired rate and for a predetermined duration of time at the site of implantation.

For implantation of a stent, an angiogram is first performed to determine the appropriate positioning for stent therapy. An angiogram is typically accomplished by injecting a radiopaque contrasting substance through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

Examples of Implantable Devices and Other Medical Devices

The various embodiments of the present invention can be used with implantable medical devices that can be implanted in a human or veterinary patient. Examples of such implantable devices are described above. Other medical devices that can be used with the various embodiments of the present invention include catheters, endocardial leads (e.g., FINE-LINE and ENDOTAK, available from Abbott Cardiovascular Systems Inc, Santa Clara, Calif.), devices facilitating anastomosis such as anastomotic connectors, and temporary indwelling devices. The underlying structure of the device can be of virtually any design.

Devices, such as stents, can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable and/or biostable polymers could also be used with the embodiments of the present invention. The device can be, for example, a bioabsorbable stent.

EXAMPLES

The examples presented in this section are provided by way of illustration of the current invention only and are not intended nor are they to be construed as limiting the scope of this invention in any manner whatsoever. Each of the examples the follows relates to the coating of 3 mm×12 mm VISION (Abbott Cardiovascular Systems Inc.) stent, which has a coatable surface area of 0.5556 cm$^2$.

Example 1

All stents were cleaned by being sonicated in isopropyl alcohol, followed by an argon plasma treatment. No primer layer was applied to the stents. Application of a coating layer on the stents was accomplished by spraying the stents with a solution of everolimus (Novartis):cRGD (Bachem, H-Gly-Pen-Gly-Arg-Gly-Asp-Ser):poly(ester-amide) at a 1:1:3 mass ratio in ethanol (anhydrous, 99.5+%, absolute ethanol). The weight % polymer in solution was 2%. The objective drug loading for each stent was 58 µg for each of the everolimus and cRGD. The poly(ester-amide) polymer used was that illustrated in FIG. 1, also referred to as PEA-40, where the subscripts X1 and X2 indicate the two constitutional units, and the p indicates multiple units. The poly(ester-amide) polymer was manufactured by standard methods. The poly (ester-amide) polymer was purified and reprecipitated several times, and there were no detectable levels, or essentially no detectable levels, of residual reactants, solvents or catalysts. The poly(ester amide) utilized had a weight-average molecular weight of in the range of about 100-120 KDa.

The spraying operation was carried out with a custom made spray coater equipped with a spray nozzle, a drying nozzle, and a means to rotate and translate the stent under the nozzles with the processing parameters outlined in Table 1. Subsequent to coating, all stents were baked in a forced air convection oven at 50° C. for 60 minutes. More than one pass under the spray nozzle was required to obtain the target weight of coating layer on the stent. The coating layer thickness was about 5-6 µm. After heat treatment of the coating, the stents were crimped onto 3.0×12 mm Xience V catheters, placed into coil to protect the catheter, and then sealed in Argon filled foil pouches. These stents were sterilized by electron beam sterilization by one pass through the electron beam at 25 KGy.

TABLE 1

| Spray Processing Parameters for Coating | |
|---|---|
| Spray Head | |
| Spray nozzle air cap, | 0.028" round |
| Spray nozzle temperature, ° C. | No heat, ambient |
| Atom pres (non-activated), psi | 15 ± 2.5 |
| Spray nozzle to mandrel dist, mm | 11 ± 1 |
| Solution flow rate, ml/hour or ml/min | 0.05 + 0.03 ml/min |
| Heat Nozzle | |
| Temperature at stent site, ° C. | 62 ± 5 |
| Air Pressure, psi | 20 ± 2 |
| Spray nozzle to mandrel distance, psi | 11 ± 1 |
| Coating Recipe(s) | |
| Spray time, seconds | 30 ± 15 |
| Dry time, seconds | 10 |
| Flow Rate and Coating Weight | |
| Target Flow Rate (ref.), µg/pass (µg solids per pass) | 18 |

Figure 2:
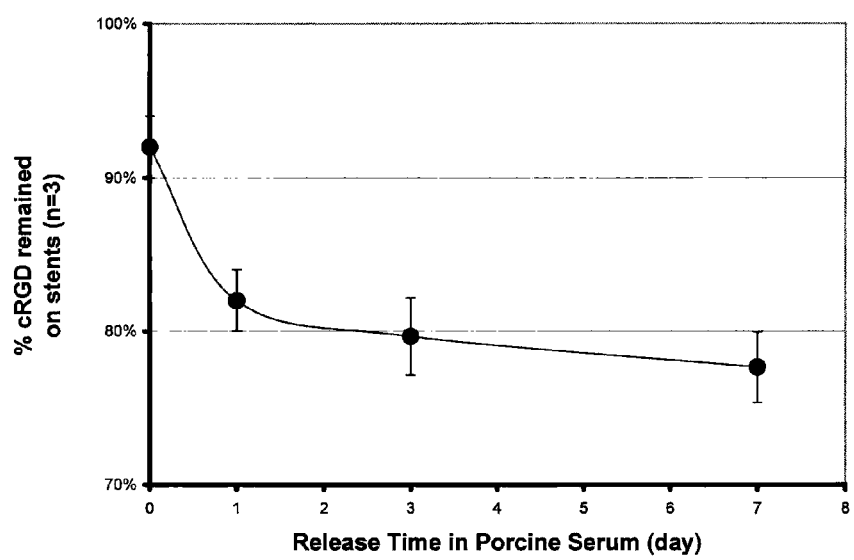
FIGS. 2 and 3 depict the amount of a cRGD protein and everolimus, respectively, retained by a stent coating including both compounds based upon an in-vitro test method.
Figure 3:
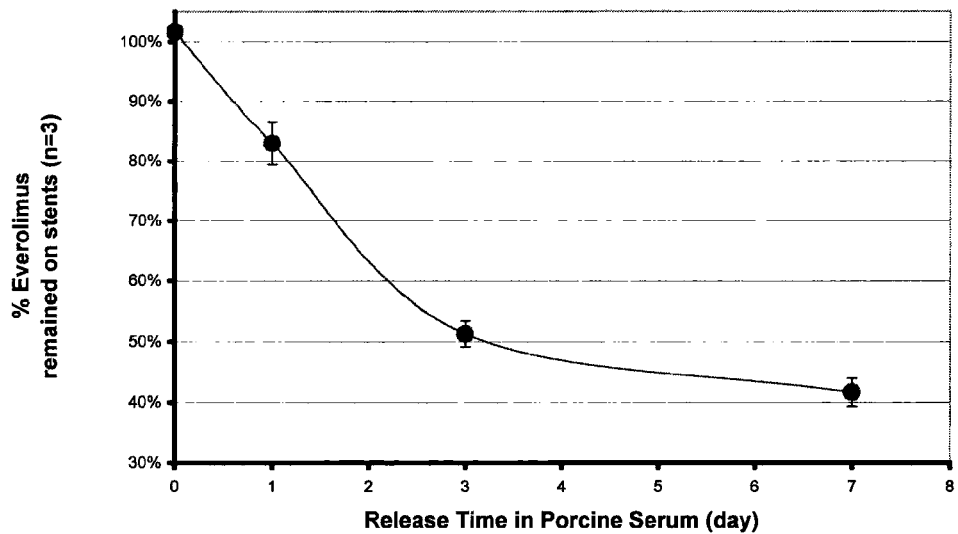

Cumulative release of both the everolimus and the cRGD peptide over 7 days was determined using an Orbit Environ Shaker. Each of nine stents were submerged in a scintillation vial containing 20 ml of Porcine Serum. At each time point, three stents were taken out and saved for extraction analysis and porcine serum solutions were discarded. The following parameter were employed Agitation: 175 rpm
Temperature: 37° C.
Release Medium: Porcine Serum with 0.3% (w/v) Sodium Azide
Time points: day 1, day 3, day 7
Media volume: 20 ml The remaining cRGD and Everolimus were extracted and analyzed by HPLC. The percent of the cRGD and the everolimus remaining in the stent based upon the objective loading of 58 μg/stent. FIGS. 2 and 3 illustrate the % of drug remaining for the N=3 stents as measured in porcine serum. The calculation of cumulative release is based upon the theoretical loading of 58 μg/stent.

Example 2

Figure 4:
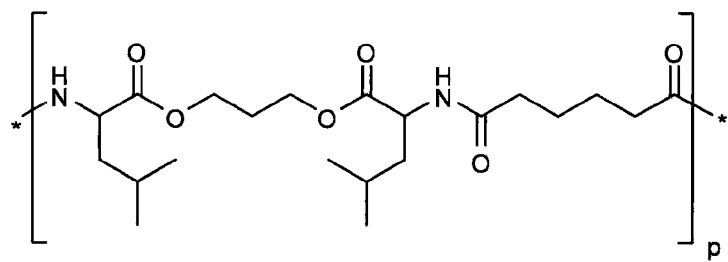
FIG. 4 is the structure of a poly(ester amide) polymer utilized in some examples provided herein.

Stents were coated as in Example 1 with the exception that a different coating solution was utilized. The stents were sprayed with a solution of everolimus:cRGD:poly(ester-amide) at a 1:1:7 mass ratio in ethanol. The weight % solids in solution was 2%. The objective drug loading for each stent was 58 μg for each of the everolimus and cRGD. The poly(ester-amide) polymer was that illustrated in FIG. 4 also referred to as PEA-11 which has only one constitutional unit, and the subscript p indicates multiples of this unit. Similar to Example 1 described above, the polymer was manufactured by standard methods and purified. The poly(ester amide) utilized had a weight-average molecular weight of about 100-120 KDa. The coating layer thickness was about 5-6 μm.

Figure 5:
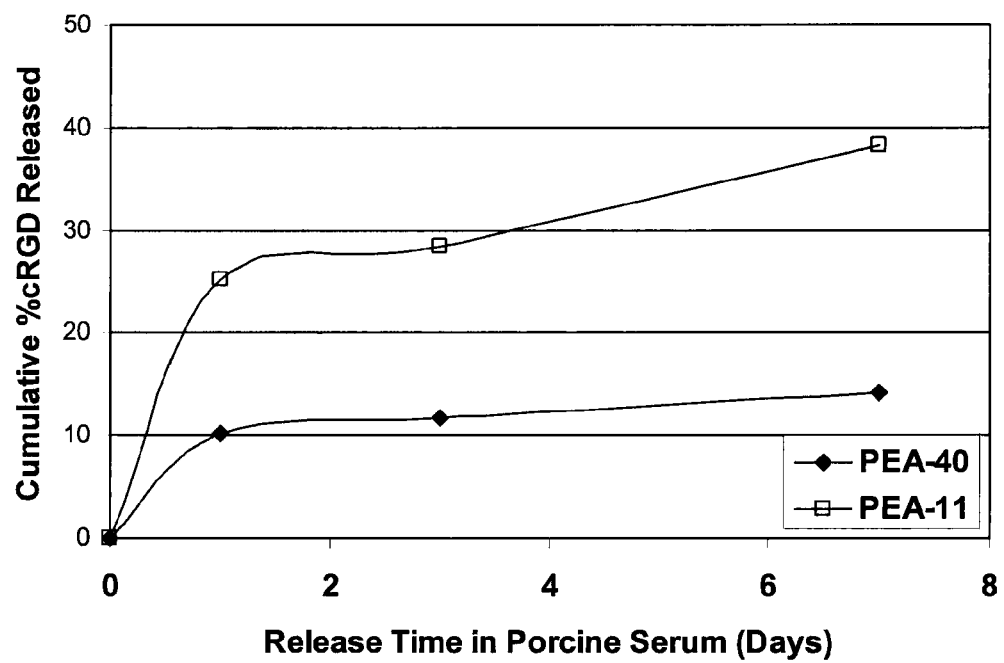
FIGS. 5 and 6 depict the cumulative release profiles of cRGD protein and everolimus, respectively, from two different stent coatings as determined by an in-vitro test method.
Figure 6:
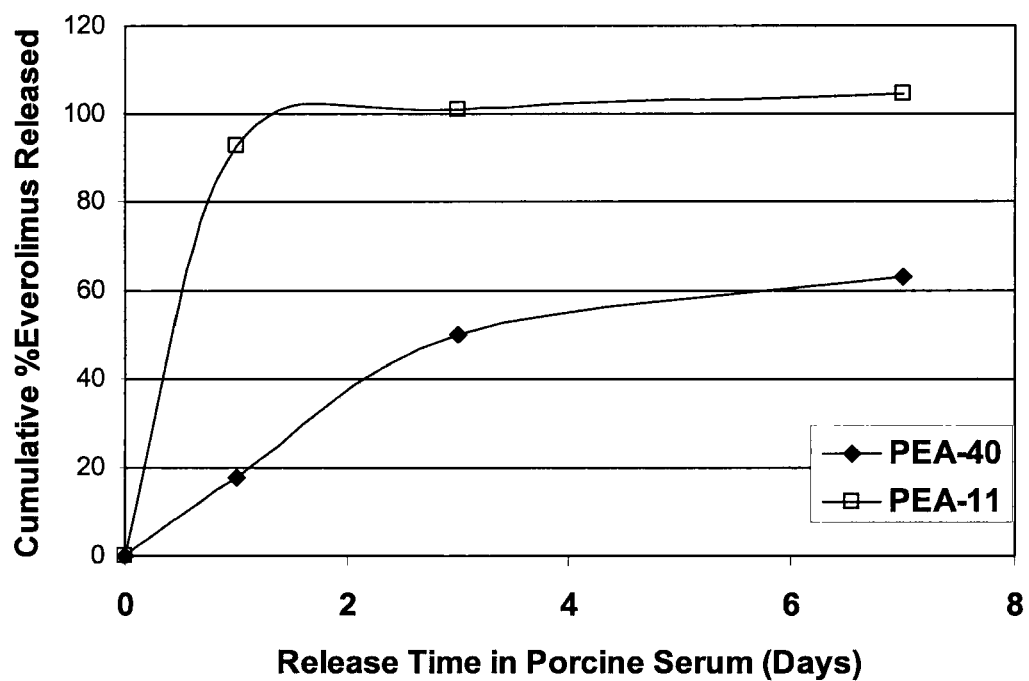

After sterilization, the stents were tested for cumulative drug release as described in Example 1. FIGS. 5 and 6 illustrate the results of the cumulative release profiles for the cRGD protein and everolimus, respectively, over 7 days for the two coating layers, that is the coating layer made with PEA-11 and the coating layer made with PEA-40. As illustrated in FIG. 6, the PEA-11 poly(ester-amide) coating layer does not provide for a sustained release of everolimus at the drug to polymer ratio used. In contrast, FIGS. 5 and 6 illustrate that the coating layer including PEA-40 provides for a sustained release profile of both everolimus and the cRGD peptide at the drug to polymer ratio used.

While particular embodiments of the present invention have been shown and described, it will be obvious to those skilled in the art that changes and modifications can be made without departing from this invention in its broader aspects. The various aspects of the invention may be used in all embodiments, and the various embodiments may be combined, when such incorporation and/or combination can be accomplished without undue experimentation. Therefore, the appended claims are to encompass within their scope all such changes and modifications as fall within the true spirit and scope of this invention.

What is claimed is:

1. An implantable medical device comprising:
a device body and a coating disposed over the device body, the coating comprising:
a drug reservoir layer comprising:
a peptide or protein;
a hydrophobic drug; and
a polymer with a weight average molecular weight between about 10 to about 150 K Daltons;
wherein the mass ratio of the peptide or protein to the hydrophobic drug is from about 1:0.1 to about 1:10;
wherein the mass ratio of the protein or peptide to the polymer is from about 1:0.1 to about 1:10;
wherein the cumulative release of the peptide or protein from the drug reservoir layer is between about 5% and about 50% at 24 hours and between about 10% and about 95% at 7 days; and
wherein the polymer is a poly(ester-amide) or a poly(amide) that is of the following formula:

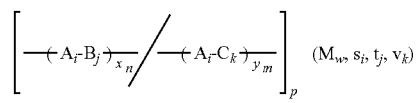

wherein:
i is an integer from 1 to 10, inclusive;
j is an integer from 0 to 10, inclusive;
k is an integer from 0 to 15, inclusive;
$x_n$ is an integer from 0 to 100, inclusive;
$y_m$ is an integer from 0 to 150, inclusive;
p is an integer from 2 to about 4500;
$M_w$ is from about 10,000 to about 1,000,000 Da;
$s_i$, $t_j$, and $v_k$ represent the average mole fraction of each of $A_i$, $B_j$, and $C_k$;
$s_i$ is a number from 0 to 0.5, inclusive;
$t_j$ is a number from 0 to 0.5, inclusive;
$v_k$ is a number from 0 to 0.5, inclusive;
with the proviso that $$\Sigma_i s_i + \Sigma_j t_j + \Sigma_k v_k = 1.0;$$

$$\Sigma_i s_i = \Sigma_j t_j + \Sigma_k v_k = 0.5;$$

$$\Sigma_i s_i > 0;$$

$$\Sigma_j t_j > 0 \text{ or } \Sigma_k v_k > 0;$$

each $A_i$ has the chemical structure:

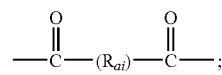

each $B_j$ has the chemical structure

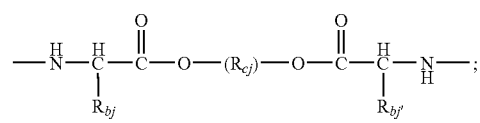

and
each $C_k$ has the chemical structure:

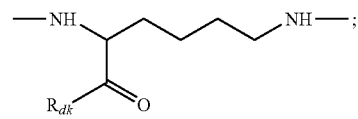

wherein:
each $R_{bj}$, and $R_{bj'}$ are independently selected from the group consisting of hydrogen and (C1-C4)alkyl, wherein:
the alkyl group is optionally substituted with a moiety selected from the group consisting of —OH, —SH, —SeH, —C(O)OH, —NHC(NH)NH$_2$,

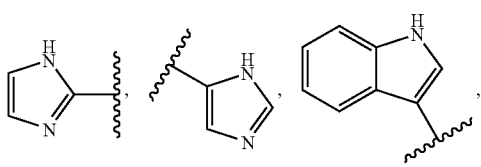

phenyl and

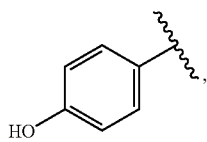

or
one or more of $R_{bj}$ and $R_{bj'}$ may form a bridge between the carbon to which it is attached and the adjacent nitrogen, the bridge comprising —$CH_2CH_2CH_2$—;
each $R_{ai}$, and each $R_{cj}$ are independently selected from the group consisting of (C1-C12)alkyl, (C2-C12)alkenyl, (C3-C8)cycloalkyl,-$(CH_2CH_2O)CH_2CH_2$— wherein q is an integer from 1 to 10, inclusive, and

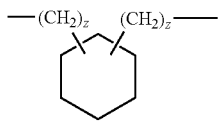

where z is 0, 1, or 2;
subject to the restriction that at least one $R_{ai}$ is selected from the group consisting of

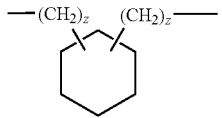

where z is 0, 1, or 2;
$R_{dk}$ is selected from the group consisting of —H, —OH, —O(C1-C20)alkyl, —O(C1C20)alkenyl and —O(CH$_2$CH$_2$O)$_w$CH$_2$CH$_2$OR$_{ek}$, wherein:
w is an integer from 1 to 600, inclusive;
$R_{ek}$ is selected from the group consisting of hydrogen, —C(O)CH=CH$_2$ and —C(O)C(CH$_3$)=CH$_2$; and,
each $R_{ai}$, corresponds to the i$^{th}$ $A_i$ group, each $R_{bj}$, $R_{bj'}$, and $R_{cj}$ corresponds to the j$^{th}$ $B_j$ group, and each $R_{dk}$ and optionally $R_{ek}$ correspond to the k$^{th}$ $C_k$ group.

2. The device of claim 1, wherein the implantable medical device is a stent.

3. The device of claim 1, wherein the cumulative release of the hydrophobic drug from the drug reservoir layer is between about 5% and about 50% at 24 hours and between about 10% and about 95% at 7 days.

4. The device of claim 1, wherein the cumulative release of the hydrophobic drug from the drug reservoir layer is between about 10% and about 35% at 24 hours and between about 25% and about 75% at 7 days.

5. The device of claim 1, wherein the mass ratio of the peptide or protein to the hydrophobic drug is from about 1:0.2 to 1:5.

6. The device of claim 1, wherein the mass ratio of the peptide or protein to the hydrophobic drug is from about 1:0.5 to 1:3.

7. The device of claim 1, wherein the mass ratio of the protein or peptide to the polymer is from about 1:0.2 to about 1:5.

8. The device of claim 1, wherein the mass ratio of the protein or peptide to the polymer is from about 1:2 to about 1:4.

9. An implantable medical device comprising:
a device body and a coating disposed over the device body, the coating comprising:
a drug reservoir layer comprising:
a peptide or protein;
a hydrophobic drug; and
a polymer with a weight average molecular weight between about 10 to about 150 K Daltons;
wherein the mass ratio of the peptide or protein to the hydrophobic drug is from about 1:0.1 to about 1:10;
wherein the mass ratio of the protein or peptide to the polymer is from about 1:0.1 to about 1:10;
wherein the cumulative release of the peptide or protein from the drug reservoir layer is between about 5% and about 50% at 24 hours and between about 10% and about 95% at 7 days;
and
wherein the polymer is a poly(ester-amide) or a poly(amide) that is of the following formula:

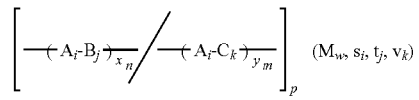

wherein:
i is an integer from 1 to 10, inclusive;
j is an integer from 0 to 10, inclusive;
k is an integer from 0 to 15, inclusive;
$x_n$ is an integer from 0 to 100, inclusive;
$y_m$ is an integer from 0 to 150, inclusive;
p is an integer from 2 to about 4500;
$M_w$ is from about 10,000 to about 1,000,000 Da;
$s_i$, $t_j$, and $v_k$ represent the average mole fraction of each of $A_i$, $B_j$, and $C_k$;
$s_i$ is a number from 0 to 0.5, inclusive;
$t_j$ is a number from 0 to 0.5, inclusive;
$v_k$ is a number from 0 to 0.5, inclusive;
with the proviso that $\Sigma_i s_i + \Sigma_j t_j + \Sigma_k v_k = 1.0$;

$\Sigma_i s_i = \Sigma_j t_j + \Sigma_k v_k = 0.5$;

$\Sigma_i s_i > 0$;

$\Sigma_j t_j > 0$ or $\Sigma_k v_k > 0$;

each $A_i$ has the chemical structure:

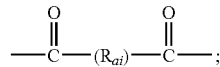

each $B_j$ has the chemical structure

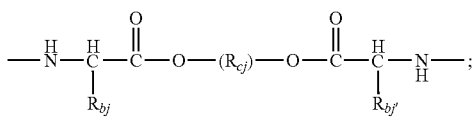

and
each $C_k$ has the chemical structure

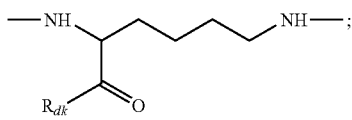

each $R_{ai}$ corresponds to the $i^{th}$ $A_i$ group, each $R_{bj}$, $R_{bj'}$ and $R_{cj}$ corresponds to the $j^{th}$ $B_j$ group, and
each $R_{dk}$ and optionally $R_{ek}$ correspond to the $k^{th}$ $C_k$ group; and
wherein i =1, j =2, k =0,
$R_{a1}$ is selected from the group consisting of —$(CH_2)_6$—, —$(CH_2)_7$—, —$(CH_2)_8$—, —$(CH_2)_9$—, and —$(CH_2)_{10}$—;
each of $R_{b1}$, $R_{b1'}$, $R_{b2}$ and $R_{b2'}$ are the same, and are selected from the group consisting of —$(CH_2)$—,—$(CH(CH_3)_2)$ and —$(CH_3)$;
$R_{c1}$ is selected from the group consisting of —$(CH_2)_4$—, —$(CH_2)_5$—, —$(CH_2)_6$—, —$(CH_2)_7$—, and —$(CH_2)_8$—;
and
$R_{c2}$ is selected from the group consisting of

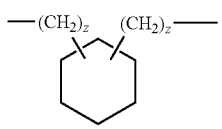

where z is 0, 1, or 2.

10. The device of claim 9, wherein for the polymer
$R_{a1}$ is —$(CH_2)_8$—;
$R_{b1}$ $R_{b1'}$, $R_{b2}$ and $R_{b2'}$ the same and are —$(CH_2)$—$(CH(CH_3)_2)$ ;
$R_{c1}$ is —$(CH_2)_6$—;
$R_{c2}$ is

and
$s_1$ is 0.5, and $t_1$ is between 0.125 and 0.375.

11. The device of claim 9, wherein the peptide or protein is cRGD, and the hydrophobic drug is everolimus.

12. The device of claim 11, wherein the mass ratio of (protein or peptide):
hydrophobic drug: polymer is about 1:1:3.

13. The device of claim 1, wherein the hydrophobic drug is selected from the group consisting of sirolimus (rapamycin), biolimus A9, deforolimus, AP23572 (Ariad Pharmaceuticals), tacrolimus, temsirolimus, pimecrolimus, zotarolimus (ABT-578), 40- O-(2-hydroxy)ethyl-rapamycin (everolimus), 40-O-(3-hydroxypropyl)rapamycin, 40-O- [2-hydroxy)ethoxy]ethyl-rapamycin, 40-O-tetrazole-rapamycin, 40-O-tetrazolylrapamycin, 40-epi-(N1-tetrazole)-rapamycin, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), dexamethasone, γ-hiridun, clobetasol, dexamethasone acetate, mometasone, imatinib mesylate, midostaurin, feno fibrate, feno fibric acid, and prodrugs thereof, co-drugs thereof, and combinations thereof.

14. The device of claim 13, wherein the hydrophobic drug is everolimus.

15. The device of claim 13, wherein the hydrophobic drug is zotarolimus.

16. The device of claim 1, wherein the hydrophobic drug is an anti-proliferative.

17. The device of claim 1, wherein the peptide or protein is selected from the group consisting of cRGD, other similar size peptides and combinations thereof.

18. The device of claim 1, wherein the peptide or protein is selected from the group consisting of RGD, an RGD peptide, a cyclic RGD peptide (cRGD), a synthetic cyclic RGD (cRGD) mimetic, or a synthetic RGD mimetic and combinations thereof 19. The device of claim 18, wherein the peptide or protein is cRGD.

20. The device of claim 1, wherein the drug reservoir layer is between about 0.5 and about 9 μm in thickness.

21. The device of claim 1, wherein the mass ratio of (protein or peptide):
hydrophobic drug: polymer is about 1:1:3.

22. An implantable medical device comprising:
a device body and a coating disposed over the device body, the coating comprising;
a drug reservoir layer comprising:
a peptide or protein;
a hydrophobic drug;
a polymer with a weight average molecular weight between about 10 to about 150 K Daltons;
wherein the mass ratio of the peptide or protein to the hydrophobic drug is about 1:0.1 to about 1:10;
wherein the ratio of the sum of the mass of peptide or protein and the mass of the hydrophobic drug to the mass of the polymer is about 1:1 to about 1:12;
wherein the drug reservoir layer thickness is between about 0.5 and about 7 μm in thickness; and
wherein the polymer is poly(ester-amide) that is a random copolymer having the formula:

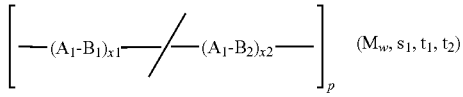

wherein:
$A_1$ has the chemical structure:

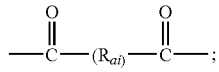

each of $B_1$ and $B_2$ has the chemical structure $$-\overset{H}{N}-\overset{H}{\underset{R_{bj}}{C}}-\overset{O}{\overset{\|}{C}}-O-(R_{cj})-O-\overset{O}{\overset{\|}{C}}-\underset{R_{bj'}}{C}-\overset{H}{N}-;$$

where $j=1$ for $B_1$ and $j=2$ for $B_2$;
$s_1$, $t_1$, and $t_2$ represent the average mole fraction of each of $A_1$, $B_1$, and $B_2$;
$t_1$ is between 0.125 and 0.375;
$t_2 = 0.5 - t_1$;
$s_1 = 0.5$; and
p is an integer from 2 to about 4500;
wherein:
$R_{a1}$ is selected from the group consisting of —$(CH_2)_6$—, —$(CH_2)_7$—, —$(CH_2)_8$—, —$(CH_2)_9$—, and —$(CH_2)_{10}$—;
each of $R_{b1}$, $R_{b1'}$, $R_{b2}$ and $R_{b2'}$ are the same, and are selected from the group consisting of —$(CH_2)$—$(CH(CH_3)_2)$ and —$(CH_3)$;
$R_{c1}$ is selected from the group consisting of —$(CH_2)_4$—, —$(CH_2)_5$—, —$(CH_2)_6$—, —$(CH_2)_7$—, and —$(CH_2)_8$—; and
$R_{c2}$ is selected from the group consisting of $$-(CH_2)_z\underset{\bigcirc}{\diagdown\diagup}(CH_2)_z-$$

where z is 0, 1, or 2.

23. The device of claim 22, wherein the hydrophobic drug is selected from the group consisting of sirolimus (rapamycin), biolimus A9, deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin, 40-O-[2-hydroxy)ethoxy]ethyl-rapamycin, 40-O-tetrazole-rapamycin, 40-O-tetrazolylrapamycin, 40-epi-(N1-tetrazole)-rapamycin, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), dexamethasone, γ-hiridun, clobetasol, dexamethasone acetate, mometasone, imatinib mesylate, midostaurin, feno fibrate, feno fibric acid, and prodrugs thereof, co-drugs thereof, and combinations thereof.

24. The device of claim 22, wherein the peptide or protein is selected from the group consisting of RGD, an RGD peptide, a cyclic RGD peptide (cRGD), a synthetic cyclic RGD (cRGD) mimetic, a synthetic RGD mimetic, other similar size peptides, and combinations thereof.

25. A method of fabricating a coated implantable medical device comprising:
providing an implantable medical device;
providing a peptide or protein, a hydrophobic drug, and a polymer with a weight average molecular weight between about 10,000 to about 150,000 Daltons;
dissolving or dispersing the peptide or protein, the hydrophobic drug, and the polymer in ethanol wherein the mass ratio of the peptide or protein to the hydrophobic drug is from about 1:0.1 to about 1:10; and wherein the mass ratio of the protein or peptide to the polymer is from about 1:0.1 to about 1:10;
applying the ethanol solution/dispersion to the implantable medical device; and
removing the ethanol to form a drug reservoir layer;
wherein the cumulative release of the peptide or protein from the drug reservoir layer is between about 5% and about 50% at 24 hours and between about 10% and about 95% at 7 days; and
wherein the polymer is a poly(ester-amide) or a poly(amide) that is of the following formula:

$$\left[\overline{\phantom{x}(A_i\text{-}B_j)_{x_n}}\Big/\overline{\phantom{x}(A_i\text{-}C_k)_{y_m}}\right]_p \quad (M_w, s_i, t_j, v_k)$$

wherein:
i is an integer from 1 to 10, inclusive;
j is an integer from 0 to 10, inclusive;
k is an integer from 0 to 15, inclusive;
$x_n$ is an integer from 0 to 100, inclusive;
$y_m$ is an integer from 0 to 150, inclusive;
p is an integer from 2 to about 4500;
$M_w$ is from about 10,000 to about 1,000,000 Da;
$s_i$, $t_j$, and $v_k$ represent the average mole fraction of each of $A_i$, $B_j$, and $C_k$;
$s_i$ is a number from 0 to 0.5, inclusive;
$t_j$ is a number from 0 to 0.5, inclusive;
$v_k$ is a number from 0 to 0.5, inclusive;
with the proviso that $\Sigma_i s_i + \Sigma_j t_j + \Sigma_k v_k = 1.0$;

$\Sigma_i s_i = \Sigma_j t_j + \Sigma_k v_k = 0.5$;

$\Sigma_i s_i > 0$;

$\Sigma_j t_j > 0$ or $\Sigma_k v_k > 0$;

each $A_i$, has the chemical structure:

$$-\overset{O}{\overset{\|}{C}}-(R_{ai})-\overset{O}{\overset{\|}{C}}-;$$

each $B_j$ has the chemical structure $$-\overset{H}{N}-\overset{H}{\underset{R_{bj}}{C}}-\overset{O}{\overset{\|}{C}}-O-(R_{cj})-O-\overset{O}{\overset{\|}{C}}-\underset{R_{bj'}}{C}-\overset{H}{N}-;$$

and
each $C_k$ has the chemical structure:

$$-NH\diagup\diagdown\diagup\diagdown NH-;$$
$$\underset{R_{dk}}{\diagdown}\diagup O$$

wherein:
each $R_{bj}$ and $R_{bj'}$ are independently selected from the group consisting of hydrogen and (C1-C4)alkyl, wherein:
the alkyl group is optionally substituted with a moiety selected from the group consisting of —OH, —SH, —SeH, —C(O)OH, —NHC(NH)NH$_2$,

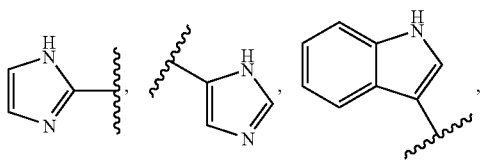

phenyl and

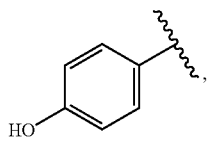

or
one or more of $R_{bj}$ and $R_{bj'}$ may form a bridge between the carbon to which it is attached and the adjacent nitrogen, the bridge comprising —CH$_2$CH$_2$CH$_2$-;
each $R_{ai}$ and each $R_{cj}$ are independently selected from the group consisting of (C1-C12)alkyl, (C2-C12)alkenyl, (C3-C8)cycloalkyl, —(CH$_2$CH$_2$O)$_q$CH$_2$CH$_2$- wherein q is an integer from 1 to 10, inclusive, and

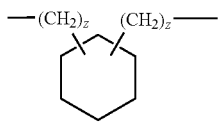

where z is 0, 1, or 2;
subject to the restriction that at least one $R_a$, is selected from the group consisting of

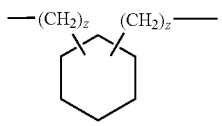

where z is 0, 1, or 2;
$R_{dk}$ is selected from the group consisting of —H, —OH, —O(C1-C20)alkyl, —O(C1-C20)alkenyl and —O(CH$_2$CH$_2$O)$_w$CH$_2$CH$_2$OR$_{ek}$, wherein:
w is an integer from 1 to 600, inclusive;
$R_{ek}$ is selected from the group consisting of hydrogen, —C(O)CH=CH$_2$ and —C(O)C(CH$_3$)=CH$_2$; and,
each $R_{ai}$, corresponds to the i$^{th}$ $A_i$ group, each $R_{bj}$, $R_{bj'}$, and $R_{cj}$ corresponds to the j$^{th}$ $B_j$ group, and
each $R_{dk}$ and optionally $R_{ek}$ correspond to the k$^{th}$ $C_k$ group.

26. The method of claim 23, wherein the cumulative release of the hydrophobic drug from the drug reservoir layer is between about 5% and about 50% at 24 hours and between about 10% and about 95% at 7 days.

27. The method of claim 23, wherein the cumulative release of the hydrophobic drug from the drug reservoir layer is between 10% and about 35% at 24 hours and between about 25% and about 75% at 7 days.

28. A coated implantable medical device fabricated by the method of claim 25.

29. The device of claim 9, wherein $R_{c2}$ is selected from the group consisting of

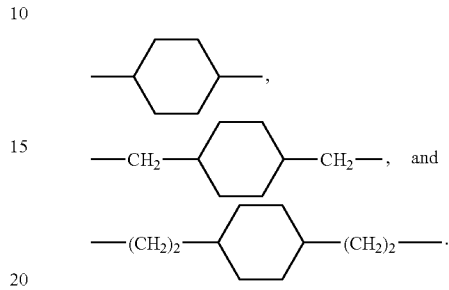

30. The device of claim 9, wherein the hydrophobic drug is selected from the group consisting of sirolimus (rapamycin), biolimus A9, deforolimus, AP23572 (Ariad Pharmaceuticals), tacrolimus, temsirolimus, pimecrolimus, zotarolimus (ABT-578), 40- O-(2-hydroxy)ethyl-rapamycin (everolimus), 40-O-(3-hydroxypropyl)rapamycin, 40-O-[2-(2-hydroxy)ethoxy]ethyl-rapamycin, 40-O-tetrazole-rapamycin, 40-O-tetrazolylrapamycin, 40-epi-(N1-tetrazole)-rapamycin, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), dexamethasone, γ-hiridun, clobetasol, dexamethasone acetate, mometasone, imatinib mesylate, midostaurin, feno fibrate, feno fibric acid, and prodrugs thereof, co-drugs thereof, and combinations thereof;
and
the peptide or protein is selected from the group consisting of RGD, an RGD peptide, a cyclic RGD peptide (cRGD), a synthetic cyclic RGD (cRGD) mimetic, a synthetic RGD mimetic, other similar size peptides, and combinations thereof.

31. A method of fabricating a coated implantable medical device comprising:
providing an implantable medical device;
providing a peptide or protein, a hydrophobic drug, and a polymer with a weight average molecular weight between about 10,000 to about 150,000 Daltons;
dissolving or dispersing the peptide or protein, the hydrophobic drug, and the polymer in ethanol wherein the mass ratio of the peptide or protein to the hydrophobic drug is from about 1:0.1 to about 1:10; and wherein the mass ratio of the protein or peptide to the polymer is from about 1:0.1 to about 1:10;
applying the ethanol solution/dispersion to the implantable medical device; and
removing the ethanol to form a drug reservoir layer;
wherein the cumulative release of the peptide or protein from the drug reservoir layer is between about 5% and about 50% at 24 hours and between about 10% and about 95% at 7 days;
and
wherein the polymer is a poly(ester-amide) or a poly(amide) that is of the following formula:

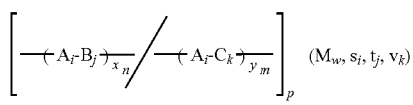

wherein:

$s_i$, $t_j$, and $v_k$ represent the average mole fraction of each of $A_i$, $B_j$, and $C_k$;

i is an integer from 1 to 10, inclusive;

j is an integer from 0 to 10, inclusive;

k is an integer from 0 to 15, inclusive;

$x_n$ is an integer from 0 to 100, inclusive;

$y_m$ is an integer from 0 to 150, inclusive;

p is an integer from 2 to about 4500;

$M_w$ is from about 10,000 to about 1,000,000 Da;

$s_i$ is a number from 0 to 0.5, inclusive;

$t_j$ is a number from 0 to 0.5, inclusive;

$v_k$ is a number from 0 to 0.5, inclusive;

with the proviso that $\Sigma_i s_i + \Sigma_j t_j + \Sigma_k v_k = 1.0$;

$\Sigma_i s_i = \Sigma_j t_j + \Sigma_k v_k = 0.5$;

$\Sigma_i s_i > 0$;

$\Sigma_j t_j > 0$ or $\Sigma_k v_k > 0$;

each $A_i$ has the chemical structure:

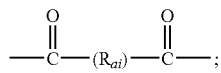

each $B_j$ has the chemical structure

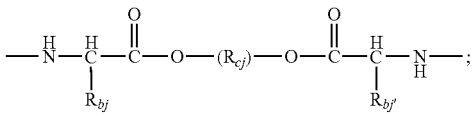

and each $C_k$ has the chemical structure:

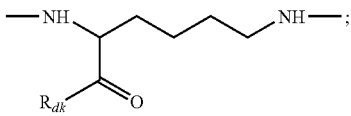

each $R_{ai}$ corresponds to the $i^{th}$ $A_i$ group, each $R_{bj}$, $R_{bj'}$, and $R_{cj}$ corresponds to the $j^{th}$ $B_j$ group, and each $R_{dk}$ and optionally $R_{ek}$ correspond to the $k^{th}$ $C_k$ group; and wherein i=1, j=2, k=0, $R_{a1}$ is selected from the group consisting of —(CH$_2$)$_6$—, —(CH$_2$)$_7$—, —(CH$_2$)$_8$—, —(CH$_2$)$_9$—, and (CH$_2$)$_{10}$—;

each of $R_{b1}$, $R_{b1'}$, $R_{b2}$ and $R_{b2'}$ are the same, and are selected from the group consisting of —(CH$_2$)—(CH(CH$_3$)$_2$) and —(CH$_3$);

$R_{c1}$ is selected from the group consisting of —(CH$_2$)$_4$—, —(CH$_2$)$_5$—, (CH$_2$)$_6$—, —(CH$_2$)$_7$—, and —(CH$_2$)$_8$—; and $R_{c2}$ is selected from the group consisting of

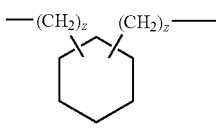

where z is 0, 1, or 2.

32. A coated implantable medical device fabricated by the method of claim 31.

\* \* \* \* \*